US006045798A

United States Patent [19]

Kapoor et al.

[11] Patent Number: 6,045,798

[45] Date of Patent: Apr. 4, 2000

[54] MEMBRANE-ASSOCIATED IMMUNOGENS OF MYCOBACTERIA

[76] Inventors: Archana Kapoor, Maison De L. Inde, 35 Boulvard Jourdan, 75014 Paris, France; Anil Munshi, 9450 Gilman Dr. No. 920573, LaJolla, Calif. 92092-0573

[21] Appl. No.: 09/099,902

[22] Filed: Jun. 18, 1998

Related U.S. Application Data

[62] Division of application No. 08/710,676, Sep. 23, 1996, Pat. No. 5,770,719, which is a division of application No. 08/192,632, Feb. 7, 1994, Pat. No. 5,559,011, which is a division of application No. 07/906,395, Jun. 29, 1992, Pat. No. 5,330,754.

[51] Int. Cl.$^{7}$ .................................................... A61K 39/00

[52] U.S. Cl. .................................... 424/190.1; 424/192.1; 424/199.1; 424/200.1; 435/252.3; 435/252.31; 435/320.1; 530/350; 536/23.1; 536/23.4; 536/23.7

[58] Field of Search ................................. 536/23.1, 23.4, 536/23.7; 435/69.1, 69.3, 252.3, 252.31, 252.33; 530/350; 424/184.1, 185.1, 190.1, 192.1, 199.1, 200.1

[56] References Cited

PUBLICATIONS

Rumschlag et al. Journal of Clinical Microbiology. vol. 28, No. 3, pp. 591–595, Mar. 1990.

Clark et al. Research in Microbiology. vol. 141, pp. 859–871, 1990.

*Primary Examiner*—Nancy Degen

*Assistant Examiner*—Remy Yucel

*Attorney, Agent, or Firm*—Richard F. Trecartin; Flehr Hohbach Test Albritton & Herbert LLP

[57] ABSTRACT

Nucleic acid encoding four novel immunodeterminant protein antigens of *M. bovis* BCG, which is a vaccine strain for tuberculosis, have been isolated. These genes were isolated as immunoreactive recombinant clones from a genomic library of *M. bovis* BCG DNA, constructed in pBR322 vector, and screened with sera collected from tuberculosis patients. The BCG DNA insert of one of the recombinants, pMBB51A, which expressed an antigen of Mr 90 kD, was sequenced completely and an ORF encoding 761 amino acids encoding a protein of deduced molecular weight 79 kD, was identified. This gene was identified to encode a membrane bound, ion-motive ATPase of *M. bovis* BCG. The approach described here can be used to identify immunogens of mycobacteria. In addition, the well-characterized *M. bovis* BCG antigens can be used in the prevention, diagnosis and treatment of tuberculosis. The 79 kD antigen is also useful in the design of recombinant vaccines against different pathogens. The sequence of the 79 kD membrane-associated polypeptides also are useful for the development of specific PCR amplification based diagnostic procedures for the detection of mycobacteria. Also, the promoter of the 79 kD antigen is useful for expressing homologous and/or heterologous antigens in mycobacteria.

10 Claims, 11 Drawing Sheets

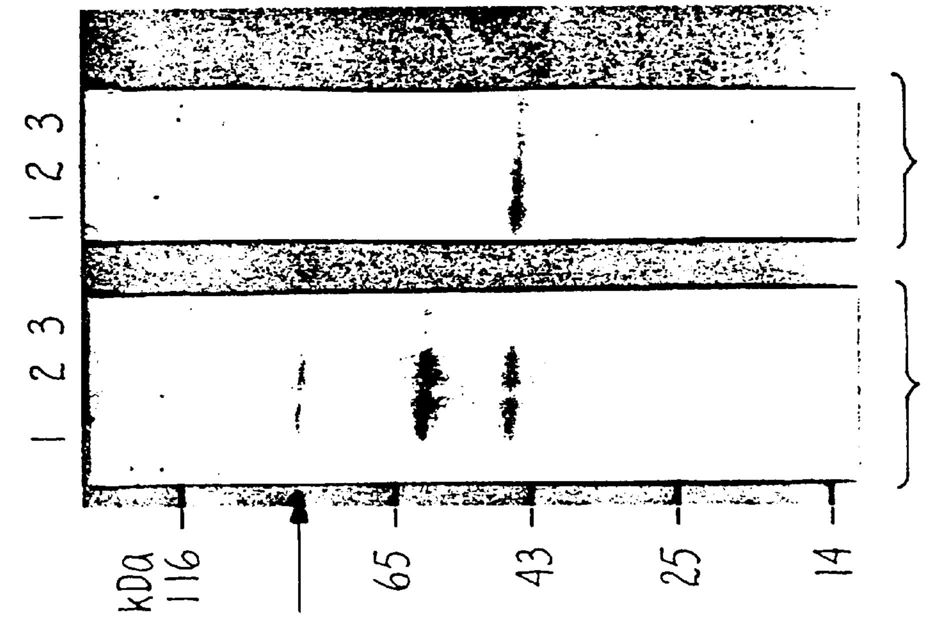
Fig. 3B
Fig. 3C
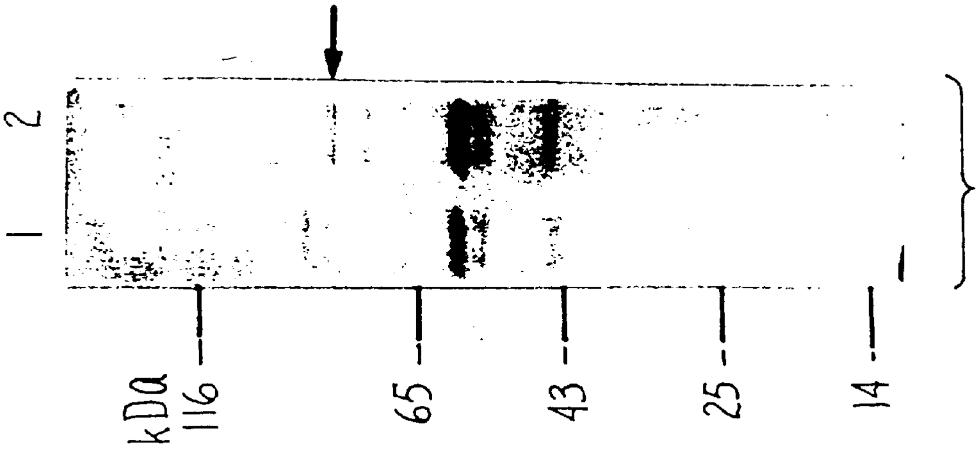
Fig. 3A

*Fig. 4A*

```
                                                                                  80
GGATCCCGCGGTCATCGATCGGGTCAAACACCGCCTCGACGGGTTCACGCTGGCGCCGCTGTCCACCGCCGCGGGAGGTG
GTGGCCGGCAGCCACGCATCTACTACGGCACCATCCTGACCGGTGACCAATACCTTCACTGCGAGCGCACCCGCAACCGG
CTGCACCACGAACTCGGCGGTATGGCCGTCGAAATGGAAGGCGGTGCGGTGGCGCAAATCTGCGCGTCCTTCGATATCCC
ATGGCTGGTCATTCGCGCGCTCTCCGATCTCGCCGGAGCCGATTCGGGGGTGGACTTCAATCGGTTTGTCGGCGAGGTGG

                                             -35                  -10        480
CGGCCAGTTCGGCCCGCGTTCTGCTGCGCTTGCTGCCGGTGTTGACGGCCTGTTGAAGACGACTATCCGCCGGTGCGTTC

ACCGCGTCAGGCGGCTTCGGTGAGGTGAGTAATTTGGTCATTAACTTGGTCATGCCGCCGCCGATGTTGAGCGGAGGCCA

                S/D       508
CAGGTCGGCCGGAAGTGAGGAGCCACG ATG ACG GCG GCC GTG ACC GGT GAA CAC CAC GCG AGT GTG
                            MET Thr Ala Ala Val Thr Gly Glu His His Ala Ser Val
                                 1

 550                                                                  600
CAG CGG ATA CAA CTC AGA ATC AGC GGG ATG TCG TGC TCT GCG TGC GCC CAC CGT GTG GAA
Gln Arg Ile Gln Leu Arg Ile Ser Gly MET Ser Cys Ser Ala Cys Ala His Arg Val Glu
                         20

                                                       650
TCG ACC CTC AAC AAG CTG CCG GGG GTT CGG GCA GCT GTG AAC TTC GGC ACC CGG GTG GCA
Ser Thr Leu Asn Lys Leu Pro Gly Val Arg Ala Ala Val Asn Phe Gly Thr Arg Val Ala
                         40

                                            700
ACC ATC GAC ACC AGC GAG GCG GTC GAC GCT GCC GCG CTG TGC CAG GCG GTC CGC CGC GCG
Thr Ile Asp Thr Ser Glu Ala Val Asp Ala Ala Ala Leu Cys Gln Ala Val Arg Arg Ala
                         60

                             750
GGC TAT CAG GCC GAT CTG TGC ACG GAT GAC GGT CGG AGC GCG AGT GAT CCG GAC GCC GAC
Gly Tyr Gln Ala Asp Leu Cys Thr Asp Asp Gly Arg Ser Ala Ser Asp Pro Asp Ala Asp
                         80

                800
CAC GCT CGA CAG CTG CTG ATC CGG CTA GCG ATC GCC GCC GTG CTG TTT GTG CCC GTG GCC
His Ala Arg Gln Leu Leu Ile Arg Leu Ala Ile Ala Ala Val Leu Phe Val Pro Val Ala
                        100
```

Fig. 4B

850 ... 900
GAT CTG TCG GTG ATG TTT GGG GTC GTG CCT GCC ACG CGC TTC ACC GGC TGG CAG TGG GTG
Asp Leu Ser Val MET Phe Gly Val Val Pro Ala Thr Arg Phe Thr Gly Trp Gln Trp Val
120

950
CTA AGC GCG CTG GCA CTG CCG GTC GTG ACC TGG GCG GCG TGG CCG TTT CAC CGC GTT GCG
Leu Ser Ala Leu Ala Leu Pro Val Val Thr Trp Ala Ala Trp Pro Phe His Arg Val Ala
140

1000
ATG CGC AAC GCC CGC CAC CAC GCC GCC TCC ATG GAG ACG CTA ATC TCG GTC GGT ATC ACG
MET Arg Asn Ala Arg His His Ala Ala Ser MET Glu Thr Leu Ile Ser Val Gly Ile Thr
160

1050
GCC GCC ACG ATC TGG TCG CTG TAC ACC GTC TTC GGC AAT CAC TCG CCC ATC GAG CGC AGC
Ala Ala Thr Ile Trp Ser Leu Tyr Thr Val Phe Gly Asn His Ser Pro Ile Glu Arg Ser 1100 180
GGC ATA TGG CAG GCG CTG CTG GGA AGC GAT GCT ATT TAT TTC GAG GTC GCG GCG GGT GTC
Gly Ile Trp Gln Ala Leu Leu Gly Ser Asp Ala Ile Tyr Phe Glu Val Ala Ala Gly Val
200

1150 ... 1200
ACG GTG TTC GTG CTG GTG GGG CGG TAT TTC GAG GCG CGC GCC AAG TCG CAG GCG GGC AGT
Thr Val Phe Val Leu Val Gly Arg Tyr Phe Glu Ala Arg Ala Lys Ser Gln Ala Gly Ser
220

1250
GCG CTG AGA GCC TTG GCG GCG CTG AGC GCC AAG GAA GTA GCC GTC CTG CTA CCG GAT GGG
Ala Leu Arg Ala Leu Ala Ala Leu Ser Ala Lys Glu Val Ala Val Leu Leu Pro Asp Gly
240

1300
TCG GAG ATG GTC ATC CCG GCC GAC GAA CTC AAA GAA CAG CAG CGC TTC GTG GTG CGT CCA
Ser Glu MET Val Ile Pro Ala Asp Glu Leu Lys Glu Gln Gln Arg Phe Val Val Arg Pro
260

1350
GGG CAG ATA GTT GCC GCC GAC GGC CTC GCC GTC GAC GGG TCC GCT GCG GTC GAC ATG AGC
Gly Gln Ile Val Ala Ala Asp Gly Leu Ala Val Asp Gly Ser Ala Ala Val Asp MET Ser
280

```
                1400
GCG ATG ACC GGC GAG GCC AAA CCG ACC CGG GTG CGT CCG GGG GGG CAG GTC ATC GGC GGC
Ala MET Thr Gly Glu Ala Lys Pro Thr Arg Val Arg Pro Gly Gly Gln Val Ile Gly Gly
                        300

1450                                                            1500
ACC ACA GTG CTT GAC GGC CGG CTG ATC GTG GAG GCG GCC GCG GTG GGC GCC GAC ACC CAG
Thr Thr Val Leu Asp Gly Arg Leu Ile Val Glu Ala Ala Ala Val Gly Ala Asp Thr Gln
                        320

                                                    1550
TTC GCC GGA ATG GTC CGC CTC GTT GAG CAA GCG CAG GCG CAA AAG GCC GAC GCA CAG CGA
Phe Ala Gly MET Val Arg Leu Val Glu Gln Ala Gln Ala Gln Lys Ala Asp Ala Gln Arg
                        340

                                        1600
CTA GCC GAC CGG ATC TCC TCG GTG TTT GTT CCC GCT GTG TTG GTT ATC GCG GCA CTA ACC
Leu Ala Asp Arg Ile Ser Ser Val Phe Val Pro Ala Val Leu Val Ile Ala Ala Leu Thr
                        360
                            1650
GCA GCC GGA TGG CTA ATC GCC GGG GGA CAA CCC GAC CGT GCC GTC TCG GCC GCA CTC GCC
Ala Ala Gly Trp Leu Ile Ala Gly Gly Gln Pro Asp Arg Ala Val Ser Ala Ala Leu Ala
                        380
                1700
GTG CTT GTC ATC GCC TGC CCG TGT GCC CTG GGG CTG GCG ACT CCG ACC GCG ATG ATG GTG
Val Leu Val Ile Ala Cys Pro Cys Ala Leu Gly Leu Ala Thr Pro Thr Ala MET MET Val
                        400
1750                                                            1800
GCC TCT GGT CGC GGT GCC CAG CTC GGA ATA TTT CTG AAG GGC TAC AAA TCG TTG GAG GCC
Ala Ser Gly Arg Gly Ala Gln Leu Gly Ile Phe Leu Lys Gly Tyr Lys Ser Leu Glu Ala
                        420
                                                    1850
ACC CGC GCG GTG GAC ACC GTC GTC TTC GAC AAG ACC GGC ACC CTG ACG ACG GGC CGG CTG
Thr Arg Ala Val Asp Thr Val Val Phe Asp Lys Thr Gly Thr Leu Thr Thr Gly Arg Leu
                        440
                                        1900
CAG GTC AGT GCG GTG ACC GCG GCA CCG GGC TGG GAG GCC GAC CAG GTG CTC GCC TTG GCC
Gln Val Ser Ala Val Thr Ala Ala Pro Gly Trp Glu Ala Asp Gln Val Leu Ala Leu Ala
                        460
```

Fig.4C

```
                              1950
GCG ACC GTG GAA GCC GCG TCC GAG CAC TCG GTG GCG CTC GCG ATC GCC GCG GCA ACG ACT
Ala Thr Val Glu Ala Ala Ser Glu His Ser Val Ala Leu Ala Ile Ala Ala Ala Thr Thr
                        480

                2000
CGG CGA GAC GCG GTC ACC GAC TTT CGC GCC ATA CCC GGC CGC GGC GTC AGC GGC ACC GTG
Arg Arg Asp Ala Val Thr Asp Phe Arg Ala Ile Pro Gly Arg Gly Val Ser Gly Thr Val
                        500

2050                                                                2100
TCC GGG CGG GCG GTA CGG GTG GGC AAA CCG TCA TGG ATC GGG TCC TCG TCG TGC CAC CCC
Ser Gly Arg Ala Val Arg Val Gly Lys Pro Ser Trp Ile Gly Ser Ser Ser Cys His Pro
                        520

                                                        2150
AAC ATG CGC GCG GCC CGG CGC CAC GCC GAA TCG CTG GGT GAG ACG GCC GTA TTC GTC GAG
Asn MET Arg Ala Ala Arg Arg His Ala Glu Ser Leu Gly Glu Thr Ala Val Phe Val Glu
                        540

                                          2200
GTC GAC GGC GAA CCA TGC GGG GTC ATC GCG GTC GCC GAC GCC GTC AAG GAC TCG GCG CGA
Val Asp Gly Glu Pro Cys Gly Val Ile Ala Val Ala Asp Ala Val Lys Asp Ser Ala Arg
                        560

                              2250
GAC GCC GTG GCC GCC CTG GCC GAT CGT GGT CTG CGC ACC ATG CTG TTG ACC GGT GAC AAT
Asp Ala Val Ala Ala Leu Ala Asp Arg Gly Leu Arg Thr MET Leu Leu Thr Gly Asp Asn
                        580

                2300
CCC GAA TCG GCG GCG GCC GTG GCT ACT CGC GTC GGC ATC GAC GAG GTG ATC GCC GAC ATC
Pro Glu Ser Ala Ala Ala Val Ala Thr Arg Val Gly Ile Asp Glu Val Ile Ala Asp Ile
                        600

2350                                                                2400
CTG CCG GAA GGC AAG GTC GAT GTC ATC GAG CAG CTA CGC GAC CGC GGA CAT GTC GTC GCC
Leu Pro Glu Gly Lys Val Asp Val Ile Glu Gln Leu Arg Asp Arg Gly His Val Val Ala
                        620

                                                        2450
ATG GTC GGT GAC GGC ATC AAC GAC GGA CCC GCA CTG GCC CGT GCC GAT CTA GGC ATG GCC
MET Val Gly Asp Gly Ile Asn Asp Gly Pro Ala Leu Ala Arg Ala Asp Leu Gly MET Ala
                        640
```

```
                                            2500
ATC GGG CGC GGC ACG GAC GTC GCG ATC GGT GCC GCC GAC ATC ATC TTG GTC CGC GAC CAC
Ile Gly Arg Gly Thr Asp Val Ala Ile Gly Ala Ala Asp Ile Ile Leu Val Arg Asp His
                        660
                            2550
CTC GAC GTT GTA CCC CTT GCG CTT GAC CTG GCA AGG GCC ACG ATG CGC ACC GTC AAA CTC
Leu Asp Val Val Pro Leu Ala Leu Asp Leu Ala Arg Ala Thr MET Arg Thr Val Lys Leu
                        680
                2600
AAC ATG GTC TGG GCA TTC GGA TAC AAC ATC GCC GCG ATT CCC GTC GCC GCT GCC GGA CTG
Asn MET Val Trp Ala Phe Gly Tyr Asn Ile Ala Ala Ile Pro Val Ala Ala Ala Gly Leu
                        700
 2650                                                             2700
CTC AAC CCC CTG GTG GCC GGT GCG GCC ATG GCG TTC TCA TCG TTC TTC GTG GTC TCA AAC
Leu Asn Pro Leu Val Ala Gly Ala Ala MET Ala Phe Ser Ser Phe Phe Val Val Ser Asn
                        720
                                                    2750
AGC TTG CGG TTG CGC AAA TTT GGG CGA TAC CCG CTA GGC TGC GGA ACC GTC GGT GGG CCA
Ser Leu Arg Leu Arg Lys Phe Gly Arg Tyr Pro Leu Gly Cys Gly Thr Val Gly Gly Pro
                        740

CAA ATG ACC GCG CCG TCG TCC GCG TGA TGCGTTGTCGGGCAACACGATATCGGGCTCAGCGGCGACCGCA
Gln MET Thr Ala Pro Ser Ser Ala TER
                                761

TCCGGTCTCGGCCGAGGACCAGAGGCGCTTCGCCACACCATGATTGCCAGGACCGCGCCGATCACCACCGGCAGATGAGT
CAAAATCCGCGTGGTGCTGACCGCGCCGGACAGCGCATCCACAATCACATAGCCGGTCAGTATGGCGACGAACGCCGTCA
GAACACCGGCCAGGCCGGCGGCGGCGCTCGGCCATAGCGCCGCGCCCACCATGATCACACCGAGCGCAATCGACCACGAC
GTGACTCGTTGAGCAAGTGGGTGCCGGCACCCGTCGGGTGCTGATGGGTCAGGCCGACGTCTAGGCCAAACCCCTGCACG
GTGCCCAGGGCGATCTGCGCGATGCCCACGCACAGCAACGCCCAACGTCGCCAGGTCATCGGTGAATGTTGCCGCCGCGG
        3250
CGCCCGGCGGATCC
```

MEMBRANE-ASSOCIATED IMMUNOGENS OF MYCOBACTERIA

This is a divisional of application Ser. No. 08/710,676 filed Sep. 23, 1996, now issued as U.S. Pat. No. 5,770,719; which is a divisional of application Ser. No. 08/192,632, filed on Feb. 7, 1994, now issued U.S. Pat. No. 5,559,011; which is a divisional of application Ser. No. 07/906,395, filed on Jun. 29, 1992, now issued U.S. Pat. No. 5,330,754.

TECHNICAL FIELD OF THE INVENTION

The invention relates to membrane-associated polypeptides of mycobacteria and, in particular, the use of such polypeptides and the nucleic acids encoding them for use as vaccines and diagnostic reagents.

BACKGROUND OF THE INVENTION

The mycobacteria are a diverse collection of acid fast, gram-positive bacteria, some of which cause important human and animal diseases. In humans, the two most common mycobacteria-caused diseases are tuberculosis (TB) and leprosy, which result from infection with *M. tuberculosis* and *M. leprae*, respectively.

Tuberculosis displays all of the principal characteristics of a global epidemic disease. Currently, tuberculosis afflicts more than 35 million individuals worldwide and results in over 4 million deaths annually. In India, at any given time, almost 8 million people are reported to suffer from this disease and 500,000 deaths recorded. These figures may not cover the totality of those suffering from this disease in this country. Thus, tuberculosis appears to be a problem of major concern in India as also in many other countries of the world.

Tuberculosis is caused by *M. tuberculosis, M. bovis, M. africanum* and *M. Microti*, the acid-fast, Gram positive, tubercle bacilli of the family Mycobacteriaceae. Some local pathogenic strains of *M. tuberculosis* have also been isolated from patients in Madras and other cities in India, which differ in some respects from *M. tuberculosis* H37Rv, which is a virulent strain.

In recent years, certain groups of individuals with AIDS have been found to have a markedly increased incidence of TB as well. It has now been shown that one group of mycobacteria which consists of *M. avium, M. intracellulare* and *M. scrofulaceum*, jointly known as MAIS complex, is responsible for disseminated disease in a large number of persons with AIDS (Kiehn et al., *J. Clin. Microbiol.*, 21:168–173 (1985); Wong et al., *Amer. J. Med.*, 78:35–40 (1985)).

Since Koch identified *M. tuberculosis* as the causative agent of tuberculosis in 1882, many scientific studies and public health efforts have been directed at diagnosis, treatment and control of this disease. However, characteristics of *M. tuberculosis* have hampered research to improve diagnosis and to develop more effective vaccines. In addition, the biochemical composition of the organism has made identification and purification of the cellular constituents difficult, and many of these materials once purified, lack sensitivity and specificity as diagnostic reagents. As a result, diagnostic and immunoprophylactic measures for mycobacterial diseases have changed little in the past half century. The conventional methods for the diagnosis of *M. tuberculosis* are troublesome and results are delayed.

Bacillus Calmette-Guerin (BCG), an avirulent strain of *M. bovis* (Calmette, A., *Masson et Cie*, Paris (1936)), is used extensively as a vaccine against tuberculosis. Though numerous studies have found that it has protective efficacy against tuberculosis (Luelmo, F., *Am. Rev. Respir. Dis.*, 125, 70–72 (1982)) BCG has failed to protect against tuberculosis in several trials (WHO, *Tech. Rep. Ser.*, 651:1–15 (1980)) for reasons that are not entirely clear (Fine, *P., Tubercle*, 65:137–153 (1984); Fine, et al., *Lancet*, (ii):499–502 (1986)).

The eradication with vaccination, early diagnosis, and efficient therapy is an important objective of the drive to combat mycobacterioses. The lacunae in the present knowledge of the biology of these pathogens—their make-up, their natural history, their physiology, biochemistry and immunological reactivities, highlights the need for attempts to unravel their weaknesses, so that more efficient ways to combat this disease can be devised. To develop more effective tools for the diagnosis and prevention of these diseases, it is important to understand the immune response to infection by mycobacterial pathogens. The mycobacterial components that are important in eliciting the cellular immune response are not yet well defined. The antibody and T-cell responses to infection or inoculation with killed mycobacteria have been studied in humans and in animals. Human patients with TB or leprosy produce serum antibodies directed against mycobacterial antigens. Although antibodies may have some function in the antimycobacterial immune response, the exact function remains to be clarified since no protective role can be ascribed to these antibodies. Protection against mycobacterial diseases involves cell-mediated immunity.

Mycobacteria do not produce any directly toxic substances and consequently their pathogenicity results from multiple factors involved in their interaction with the infected host. Intracellular parasitism probably depends on host cell trophic factors; it is conceivable that their short supply may be bacteriostatic and could play a role in the mechanism of mycobacterial dormancy.

It is generally understood that protective immunity in mycobacterial infection is mediated by specific T cells which activate macrophages into non-specific tuberculocidal activity. Evidence suggests that gamma-IFN triggers macrophages towards $H_2O_2$-mediated bacterial killing, but related or other macrophage activating factor (MAF) molecules may also be involved. The causes responsible for the inadequate bactericidal function at sites of abundant T cell proliferation have not yet been explained. Dissociation between delayed-type hypersensitivity (DTH) and protective immunity led to views that T-cells of a distinct subset or specificity could be responsible for the acquired resistance to mycobacterial infection. Alternatively, interference with protection may result from corollary cellular reactions, namely by suppressor T-cells and macrophages, or from the shifting of T-cells towards helper function for B-cells.

Unlike viral and some parasite pathogens which can evade host resistance by antigenic shift, mycobacteria have a resilient cell wall structure and can suppress host immune responses by the action of their immunomodulatory cell wall constituents. Whilst the success of protective immunization towards other microbial pathogens mainly depends on quantitative parameters of immunity, it appears that mycobacterial immunomodulatory stimuli produce a regulatory dysfunction of the host immune system. This may not be possible to override simply by more resolute immunization using vaccines of complex composition such as whole mycobacteria (e.g. BCG). Perhaps mycobacteria did not evolve potent "adjuvant" structures to boost the host immunity but rather to subvert host defenses towards ineffective cellular reactions operating to the advantage of the pathogen.

Vaccination with an attenuated pathogen such as BCG could amplify further immune responses but with limited protection of the host, the potential scope for immunization with defined antigens is yet to be explored.

The purification and characterization of individual antigenic proteins are essential in understanding the fundamental mechanism of the DTH reaction on the molecular level. The possible functional role of proteins of defined structure in the pathogenesis of mycobacterial diseases as well as for diagnostic purposes remains of great interest. Numerous groups have attempted to define mycobacterial antigens by standard biochemical and immunological techniques, and common as well as species specific-antigens have been reported in mycobacteria (Minden, et al., *Infect. Immun.*, 46:519–525 (1984); Closs, et al., *Scand. J. Immunol.*, 12:249–263 (1980); Chaparas, et al., *Am. Rev. Respir. Dis.*, 122:533 (1980); Daniel, et al., *Microbiol. Rev.*, 42:84–113 (1978); Stanford, et al., *Tubercle*, 55:143–152 (1974); Kuwabara, S., *J. Biol. Chem.*, 250:2556–2562 (1975)).

Very little information about the mycobacterial genome is available. Initially, basic studies were conducted to estimate the genome size, G+C content and the degree of DNA homology between the various mycobacterial genomes (Grosskinsky, et al., *Infect. Immun.*, 57, 5:1535–1541 (1989); Garcia, et al., *J. Gen. Microbiol.*, 132:2265–2269 (1986); Imaeda, T., *Int. J. Sys. Bacteriol.*, 35, 2:147–150 (1985); Clark-Curtiss, et al., *J. Bacteriol.*, 161 3:1093–1102 (1985); Baess, I. et al., B., *Acta. Path. Microbiol. Scand.*, (1978) 86:309–312; Bradley, S. G., *Am. Rev. Respir. Dis.*, 106:122–124 (1972)). Recently, recombinant DNA techniques have been used for the cloning and expression of mycobacterial genes. Genomic DNA fragments of *M. tuberculosis, M. leprae* and some other mycobacterial species were used for the construction of lambda gtll phage (Young, et al., *Proc. Natl. Acad. Sci.*, U.S.A., 82:2583–2587 (1985); Young, et al., *Nature* (London), 316:450–452 (1985)) or other vector-based recombinant gene libraries. These libraries were screened with murine monoclonal antibodies (Engers, et al., *Infect. Immun.*, 48:603–605 (1985); Engers, et al., *Infect. Immun.*, 51:718–720 (1986)) as well as polyclonal antisera and some immunodominant antigens were identified. The principal antigen among these being five 12, 14, 19, 65 & 71 kDa of *M. tuberculosis* (Young et al., *Proc. Natl. Acad. Sci.*, U.S.A., 82:2583–2587 (1985); Shinnick et al., *Infect. Immun.*, 55(7):1718–1721 (1987); Husson and Young, *Proc. Natl. Sc. Acad.*, 84:1679–1683 (1987); and five 12, 18, 23, 36 & 65 kDa antigens of *M. leprae* (Young, et al., *Nature*(London), 316:450–452 (1985)). A few homologues of some of these antigens were also identified in some other mycobacterial species (e.g., BCG) (Yamaguchi et al., *FEB* 06511, 240:115–117 (1988); Yamaguchi et al., *Infect. Immun.*, 57:283–288 (1989); Matsuo, et al., *J. Bacteriol.*, 170, 9:3847–3854 (1988); Radford, et al., *Infect. Immun.*, 56, 4:921–925 (1988); Lu, et al., *Infect. Immun.*, 55, 10:2378–2382 (1987); Minden, et al., *Infect. Immun.*, 53, 3:560–564 (1986); Harboe, et al., *Infect. Immun.*, 52, 1:293–302 (1986); Thole, et al., *Infect. Immun.*, 50, 3:800–806 (1985)). These antigens, however, are either intracellular or secreted molecules.

Although *M. bovis* BCG has been widely used as a vaccine against tuberculosis, the determination of the membrane-associated polypeptides of mycobacterium that are capable of inducing a protective immune response is highly desirable. The use of such a membrane-associated polypeptide or the DNA encoding it provides for the generation of recombinant vaccines, e.g., mycobacterial membrane-associated immunogens expressed in, for example, a virus or bacterium such as vaccinia virus, Salmonella, etc. used as a live carrier, or the display of non-mycobacterial immunogens on the surface of a cultivable mycobacterial strain which can be used as a live recombinant vaccine.

Accordingly, it is an object herein to provide methods for identifying and isolating nucleic acids encoding a membrane-associated polypeptide of mycobacteria.

Further, it is an object herein to provide membrane-associated polypeptides of mycobacteria and the nucleic acids encoding it.

Still further, it is an object herein to provide vaccines utilizing all or part of the membrane-associated polypeptide of a mycobacterium or the DNA encoding such membrane-associated polypeptide.

Still further, it is an object to provide reagents comprising said membrane-associated polypeptide with a mycobacterium or DNA encoding it useful in diagnostic assays for mycobacterial infection.

Still further, it is an object to provide a promoter sequence comprising the promoter of said membrane associated polypeptide, which can direct gene expression in mycobacteria as well as in other microorganisms such as *E. coli.*

SUMMARY OF THE INVENTION

In accordance with the foregoing objects, the invention includes compositions comprising nucleic acid encoding all or part of a membrane-associated polypeptide of a mycobacterium and the membrane-associated polypeptide encoded by said DNA. The membrane-associated polypeptide is characterized by the ability to detect an immune response to pathogenic mycobacteria or the mycobacteria from which the membrane associated polypeptide or part thereof is derived. Such mycobacteria include *M. bovis, M. tuberculosis, M. leprae, M. africanum* and *M. microti, M. avium, M. intracellular* and *M. scrofulaceum* and *M. bovis* BCG.

A particular mycobacterial membrane-associated polypeptide is a 79 kD ion-motive ATPase. Extra-cellular, intra-cellular and transmembrane domains are identified in this mycobacterial membrane-associated polypeptide based upon its DNA and deduced amino acid sequence.

The invention also includes vaccines utilizing all or part of a membrane-associated mycobacterial polypeptide or an expressible form of a nucleic acid encoding it. The invention also includes mycrobacterial promoter sequences capable of directing gene expression in mycobacteria as well as in other microorganisms such as *E. coli.* Such promoters are from mycobacterial genes encoding membrane-associated ATPases. A preferred promoter is that of the gene encoding the *M. bovis* BCG 79 kD membrane-associated polypeptide. This promoter sequence is especially useful to express genes of interest in mycobacteria.

BRIEF DESCRIPTION OF THE DRAWINGS

FIGS. 3A–3C illustrate the results of Western blot analysis of the sonicated supernate of recombinant clone pMBB51A which carries a BCG DNA insert identified following immunoscreening of the recombinant colonies. The top panel shows reactivity of MBB51A (lane 2) and *E. coli* (lane 1) with sera from TB patients. The bottom panel (part A) shows reactivity of MBB51A (lanes 1 and 2) and *E. coli* (lane 3) with anti-H37Rv sera raised in rabbits. Part B shows reactivity of MBB51A (lanes 1 and 2) and *E. coli* (lane 3) with the second antibody alone. Arrows indicate the position of the 90 kD immunoreactive BCG protein expressed by the recombinant MBB51A, which was absent in the negative control.

FIGS. 4A–4C illustrate the nucleotide sequence (Seg. ID No.: 1) of clone pMBB51A 3.25 kb insert DNA containing the *M. bovis* BCG immunoreactive MBB51A gene encoding an ion-motive ATPase, with a deduced molecular weight of 79 kD. The deduced amino acid sequence (Seq. ID No.: 2) is shown below the nucleotide sequence. Upstream promoter elements are underlined. Transcription termination region is indicated by inverted arrows. 5' and 3' flanking regions are also shown.

DETAILED DESCRIPTION OF THE INVENTION

As used herein, a "membrane-associated polypeptide" of a mycobacterium is defined as any Mycobacterial membrane-associated polypeptide which is capable of detecting an immune response against the wild-type mycobacterium containing the membrane-associated polypeptide. However, based upon the observed cross-reactivity of the 79 kD membrane-associated polypeptide of an *M. bovis* BCG with pooled anti-sera from patients afflicted with tuberculosis and the cross-hybridization as between the DNA encoding the 79 kD membrane-associated polypeptide and the DNA of *M. tuberculosis* H37Rv, the membrane-associated polypeptide of the invention is not limited to that identified herein from *M. bovis* BCG. Rather, it encompasses not only homologs to the 79 kD ion-motive ATPase but also any and all membrane-associated polypeptides of a mycobacterium that can be used to detect an immune response by the same or a different mycobacteria in which the membrane-associated polypeptide is normally found.

As used herein, "nucleic acid" includes DNA or RNA as well as modified nucleic acid wherein a detectable label has been incorporated or wherein various modifications have been made to enhance stability, e.g., incorporation of phosphorothioate linkages in the phosphoribose backbone, etc. Such nucleic acid also includes sequences encoding the anti-sense sequence of the DNA encoding the membrane-associated polypeptide such that the now well-known anti-sense technology can be used to modulate expression of such membrane-associated polypeptides.

In some aspects of the invention, the nucleic acid sequence encoding all or part of a membrane-associated polypeptide of the mycobacterium is used as a vaccine.

Figure 5:
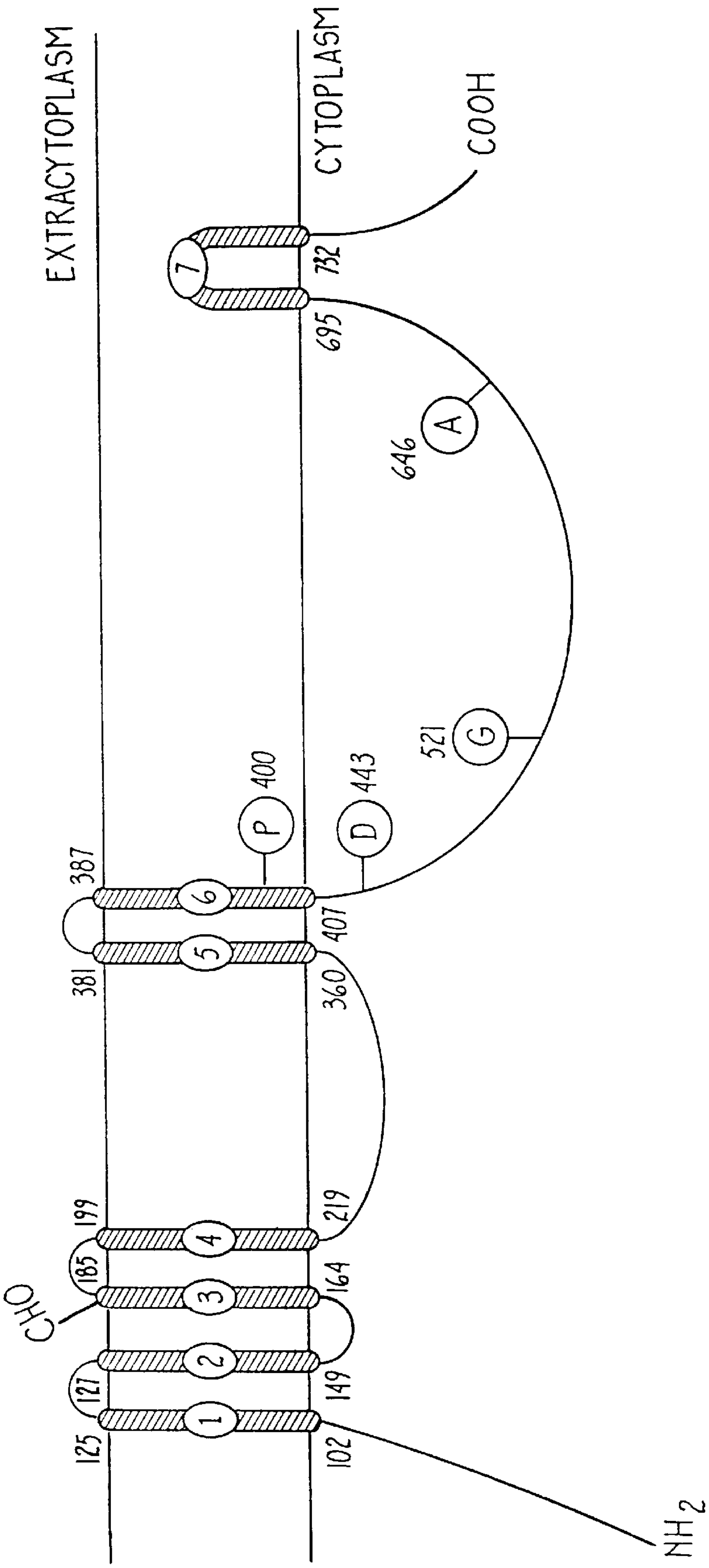
FIG. 5 illustrates a schematic model derived for the 79 kD protein encoded by pMBB51A which represents an ion-motive ATPase of BCG. The model considers only the structural and functional features that are prominent in the other ion-motive ATPase homologs of transmembrane domains of the protein. Functionally, important amino acid residues are indicated (P), proline at position 400; (D), aspartic acid at position 443; (G), glycine at position 521; and (A), alanine at position 646. Numbers indicate amino acid residues broadly defining the limits of the transmembrane domains.

When so-used the nucleic acid is generally an "expressible nucleic acid" that contains all necessary expression regulation sequences to control transcription and translation of the nucleic acid in a designated host system. In some vaccine embodiments, the DNA encodes a chimeric polypeptide containing at least one transmembrane domain of the membrane-associated polypeptide and an "immunogenic polypeptide". The transmembrane domain is used to display the immunogenic polypeptide on the surface of a particular host organism such as an attenuated live vaccine. When the membrane-associated polypeptide includes more than one transmembrane region, one or more of the transmembrane regions can be used with an immunogenic polypeptide. Thus, for example, the 79 kD ion-motive ATPase as shown in FIG. 5 has at least three extracellular domains into which an immunogenic polypeptide can be engineered by well-known methods involving recombinant DNA technology. Although it is preferred that more than one transmembrane region be used to display an immunogenic polypeptide, one skilled in the art can readily vary the length of such a membrane-associated polypeptide to maximize an immunogenic response or to minimize the amount of membrane-associated polypeptide used in such applications.

As used herein, "immunogenic polypeptide" comprises all or part of any polypeptide which can potentially be utilized in a vaccine or diagnostic application. Thus, the immunogenic polypeptide can comprise heterologous immunogens, i.e., immunogens from non-mycobacterial sources, e.g., Salmonella or Shiqella or from different mycobacteria from which the membrane-associated polypeptide is derived, e.g., immunogens from *Mycobacterium tuberculosis* fused to a membrane-associated polypeptide from *M. bovis* BCG. However, in some instances homologous immunogens can be used. For example, each of the extracellular domains as set forth in FIG. 5 herein can be combined and displayed by combination with one or more of the transmembrane domains from the membrane-associated polypeptide normally containing them. Alternatively, the intercellular domains can be displayed extracellularly using appropriate transmembrane regions from the same molecule.

In an alternate vaccine embodiment, all or part of the membrane-associated polypeptide of mycobacteria, rather than the DNA encoding, is used as part of a vaccine. Such proteinaceous vaccines are formulated with well-known adjuvants and administered following well-established protocols known to those skilled in the art.

In still other embodiments, the nucleic acid encoding the membrane-associated polypeptide of the invention can be used as a diagnostic for detecting infection based upon hybridization with wild-type genes contained by the infectious mycobacterium. Such detection can comprise direct hybridization of DNA extracted from an appropriate diagnostic sample or PCR amplification using the nucleotide sequence of the nucleic acid encoding the membrane-associated polypeptide of the invention to prime amplification. If PCR amplification is primed in a conserved region the presence of mycobacteria in a diagnostic sample can be determined. If primed in a non-conserved region which is species specific the diagnostic assay determined the specific mycobacterium causing an infection.

In addition, the membrane-associated polypeptide of the invention can also be used to detect the presence of antibodies in the sera of patients potentially infected with mycobacteria. Such detection systems include radioimmunoassays and various modifications thereof which are well-know to those skilled in the art. In addition, the membrane-associated polypeptide of the invention can be used to detect the presence of a cell-mediated immune response in a biological sample. Such assay systems are also well-known to those skilled in the art and generally involve the clonal expansion of a sub-population of T cells responding to stimuli from the membrane-associated polypeptide. When so-used, the humoral and/or cell-mediated response of a patient can be determined and monitored over the course of the disease.

Recombinant clones encoding immunogenic protein antigens of *M. bovis* BCG have been isolated from a genomic library of *M. bovis* BCG DNA. In particular, DNA fragments encoding four protein antigens of *M. bovis* BCG have been isolated by probing a pBR322 library of *M. bovis* BCG DNA with sera from TB patients, absorbed on *E. coli*. Restriction site maps of these four recombinant clones are different from those of the five immunodominant antigens of mycobacteria (Young, et al., *Proc. Natl. Acad. Sci*., U.S.A., 82:2583–2587 (1987); Husson and Young, *Proc. Natl. Acad. Sci*., U.S.A., 84:1679–1683 (1987); Shinnick et al., *Infect. Immun*., 55:1718–1721 (1987)), thereby indicating that these cloned protein antigens are novel. One of the recombinant DNA clones encoded an immunoreactive protein with apparent molecular weight of 90 kD as determined by Western blot analysis. The complete nucleotide sequence of the insert DNA of this clone was determined. This clone was found to carry a mycobacterial promoter and a monocistronic ORF encoding a protein of 761 amino acids with a deduced molecular weight of 79 kD. This 79 kD protein had extensive homology with ion-motive ATPases of *S. faecalis* (Solioz et al., *J. Biol. chem*, 262:7358–7362 (1987)), *E. coli* (Hesse et al., *Proc. Natl. Acad. Sci*., U.S.A., 81:4746–4750 (1984)) and several other organisms, and thus, represents an ion-motive ATPase or a putative K+ATPase of BCG. Using computer algorithms, this ion-motive ATPase was determined to be a membrane protein and has a homologue in *M. tuberculosis* H37Rv, which is pathogenic in humans, but not in *M. vaccae* and *M. smegmatis*, which are non-pathogenic. As a result, novel BCG immunogens can be available which can be useful in the prevention, diagnosis and treatment of tuberculosis and other mycobacterial infections. They can be used, for example, in the development of highly specific serological tests for screening patients for individuals producing antibodies to *M. tuberculosis*, or those infected with *M. tuberculosis*, in the development of vaccines against the disease, and in the assessment of the efficacy of the treatment of infected individuals.

Further, based on the nucleotide sequence of the pMBB51A insert DNA, appropriate oligonucleotide primers can be used for PCR amplification using as template *M. bovis* BCG or *M. tuberculosis* H37Rv DNA. Such a PCR amplification scheme can be thus useful for the detection of mycobacterial DNA in a given sample. Further, by a judicious choice of the primer design, such an amplification procedure can be adapted for taxonomic classification of mycobacterial DNAs. For example, using primers to flank a heavily conserved region such as the ATP-binding site, PCR amplification is common to all mycobacterial species, whereas using primers from non-conserved areas, amplification can be made species specific.

EXAMPLE I

Isolation and Characterization of Genes Encoding Immogenic Protein Antigens of *Mycobacterium bovis* BCG and *Mycobacterium tuberculosis* H37R A. Construction of Recombinant DNA Libraries of *M. bovis* BCG DNA and *Mycobacterium tuberculosis* H37Rv A recombinant DNA library of *M. bovis* BCG genomic DNA was constructed using pBR322 a high copy number plasmid vector (Bolivar, et al., *Gene*, 2:95–113 (1977)) with antibiotic markers (ampicillin and tetracycline) and several unique cloning sites. *M. bovis* BCG cells were harvested from a culture in late logarithmic phase of growth and high molecular weight DNA was isolated by the procedure of (Eisenach, et al., *J. Mol. Biol*., 179:125–142 (1986)) with slight modifications. BCG DNA was digested to completion with BamH I and shotgun cloning of these fragments into the BamH I site of pBR322 was performed. The genomic library was transformed into *E. coli* strain DHI and recombinants were scored on the basis of ampicillin resistance and tetracycline sensitivity. The aim of this approach was to generate restriction fragments of a broad size range so as not to restrict the library to DNA fragments of any particular size range. This cloning strategy also ensured to a large extent that any recombinants selected for expression of mycobacterial antigens should be likely to drive expression from a mycobacterial promoter rather than the Tet promoter of pBR322.

The BCG library constructed in this manner contained 2051 clones of BCG origin. In an analogous manner, a genomic library of *Mycobacterium tuberculosis* H37Rv DNA was constructed and 1100 clones obtained.

The BCG DNA inserts ranged in size from 0.9 to 9.5 kb. The average size of the mycobacteria DNA fragments inserted in pBR322 was estimated to be about 4 kb. Given the genome size of BCG to be $4.5 \times 10^3$ kb (Bradley, S. G., *J. Bacteriol*., 113:645–651 (1973); Imaeda, et al., *Int. J. Syst. Bacteriol*., 32, 456–458 (1982)), about 1000 clones of this average insert size would represent comprehensively the entire genome of the microorganism.

B. Isolation of Recombinant DNA Clones Encoding BCG *Mycobacterium bovis* BCG and *Mycobacterium tuberculosis* H37Rv Protein Antigens In order to identify recombinants expressing mycobacterial antigens, a colony immunoscreening assay (CIA) to screen recombinant colonies with appropriate antisera, was established. Sera obtained from 20 patients newly diagnosed with active pulmonary tuberculosis were pooled for use in immunoscreening. None of the patients had received treatment for tuberculosis prior to this study and their sputa were positive for acid fast bacteria in all cases. Pooled sera were absorbed on a *E. coli* sonicate overnight at 4° C., to eliminate antibodies cross-reactive to *E. coli* antigens, thereby improving signal to noise ratio during the immunoscreening.

Figure 1A:
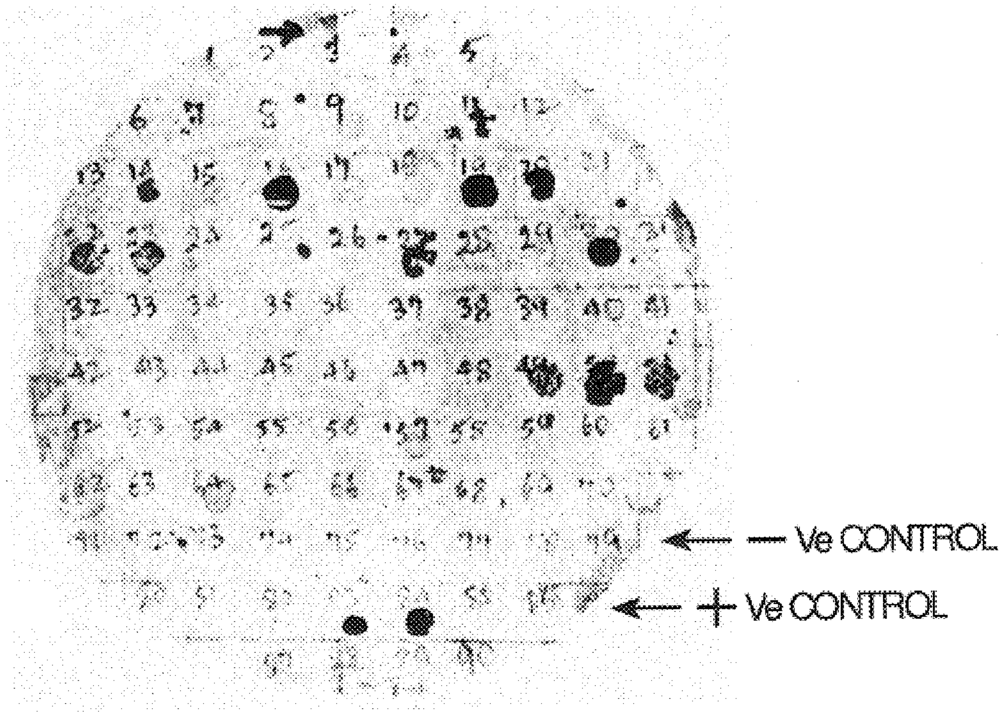
FIGS. 1A and 1B illustrate the results of immunoscreening of recombinant colonies carrying *M. bovis* BCG DNA (panel A) and *M. tuberculosis* H37Rv DNA (panel B), using sera from TB patients in which the presence of *M. bovis* BCG antigens and *M. tuberculosis* H37Rv antigens capable of reacting with the antisera is indicated by a qualitative signal.
Figure 1B:
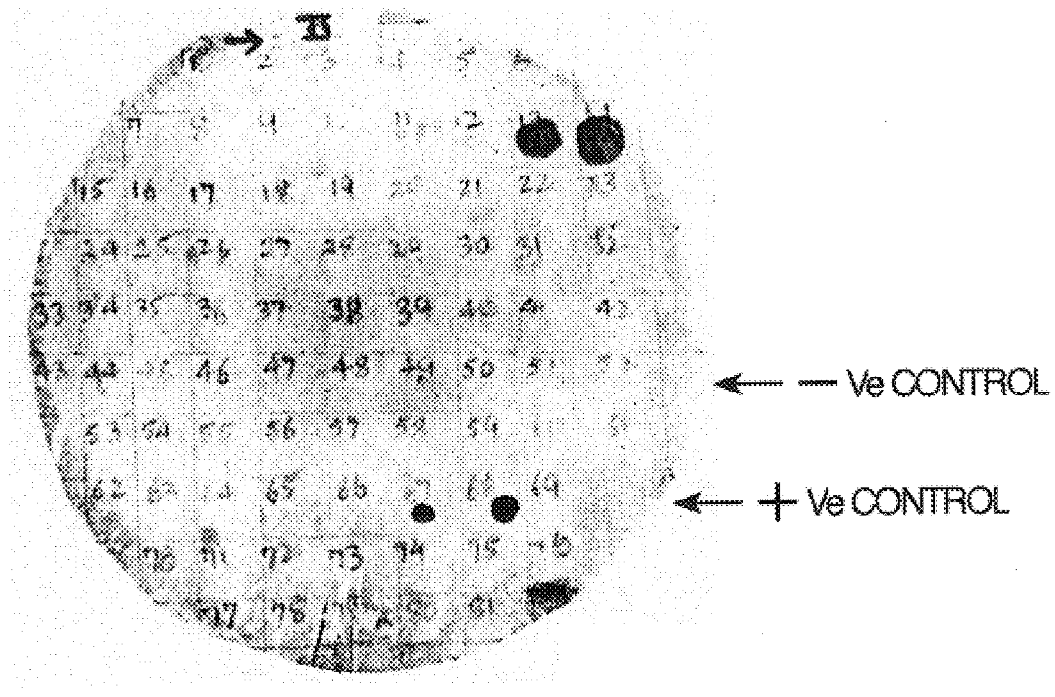

Individual recombinant colonies were grown overnight on nitrocellulose membranes and immunoscreening was carried out as described with slight modifications. The colonies were lysed in chloroform vapor to release the cloned mycobacterial antigens, immobilized on the nitrocellulose paper. The immobilized antigens were reacted with TB sera and binding of the antibody was revealed by standard procedures using a horseradish peroxidase-protein A detection system. The signals obtained with the recombinant clones were compared with that obtained in case of *E. coli* colonies harbouring pBR322 vector alone, which served as the negative control, to assess the signal to noise ratio. Further, to ascertain whether the immunoreactivity of the recombinant clones was due to anti-mycobacterial antibodies or due to a reaction with normal serum components, another CIA of the selected recombinants was performed using TB sera and normal human sera NHS which had been absorbed on *E. coli* in a manner analogous to that described earlier for TB sera. Only those clones reacting selectively with TB sera and not with NHS, were considered to be unambiguously suggestive of the presence of mycobacterial antigens. The use of this immunoscreening approach to identify recombinant colonies carrying mycobacterial DNA inserts capable of expressing mycobacterial antigens is described below:

FIG. 1 shows the result of immunoscreening of recombinant colonies carrying *M. bovis* BCG DNA (panel A) or *M. tuberculosis* H37 Rv DNA (panel B) using sera from TB patients. The colonies were grown on nitrocellulose paper overnight, lysed to release the cloned mycobacterial antigen and allowed to react with the antibodies. The presence of mycobacterial antigen is indicated by a qualitative signal in the recombinant clones which is absent in the negative control comprising colonies harbouring pBR322 vector alone. A similar assay was repeated with normal human serum to ascertain the specificity of the cloned mycobacterial antigens. 51 recombinant colonies carrying *M. bovis* BCG DNA inserts and 45 recombinant colonies carrying *M. tuberculosis* H37Rv DNA inserts were screened by the above procedure; 14 clones of BCG origin (panel A) and 2 clones of H37Rv origin (panel B) exhibited distinct strong signals indicating the immunoreactivity of these clones (FIG. 1). All these clones were also tested for immunoreactivity with NHS. However, with the exception of 3 clones which showed a slight reactivity to NHS, none of the clones reacted with NHS, thereby indicating that these expressed mycobacterial antigens reacted selectively with TB sera. Thus, this procedure resulted in the forthright identification of recombinant clones encoding mycobacterial antigens. This strategy can be generally applicable to mycobacterial gene banks prepared in plasmid or cosmid vectors to identify genes which are expressed in *E. coli* at least to the limit detectable by the immunoassay.

Figure 2A:
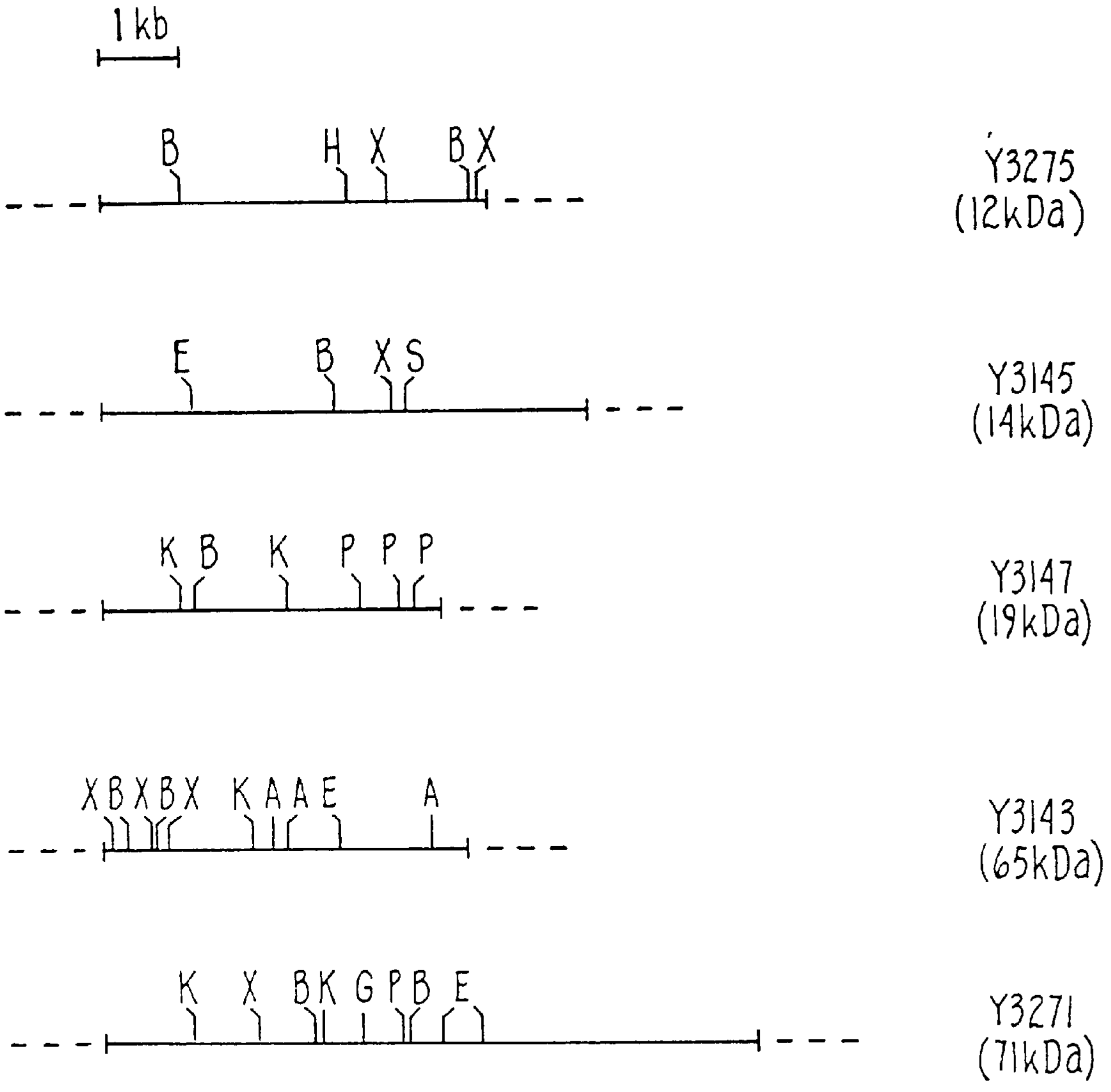
FIGS. 2A and 2B show the comparison of restriction site maps of recombinant clones carrying BCG DNA identified using the immunoscreening assay described herein (panel B) with the restriction site maps of five immunodominant antigens of *M. tuberculosis* and *M. bovis* BCG genomic DNAs, respectively, (Husson and Young, *Proc. Natl. Acad. Sci*., U.S.A., 84:1679–1683 (1987); Shinnick et al., *Infect. Immun*., 55:1718–1721 (1987) (panel A)). Restriction maps in each panel have been drawn to the same scale (indicated at the top), and restriction sites are indicated above the restriction maps. The dotted line in panel A represents the non-mycobacterial DNA. Restriction enzymes: B, BamHI, E, EcoRI, G, BglII, K, KpnI, P, PvuI, X, XhoI, H,HincII, U, PvuII, Ps, PstI, Hi, HindIII. In panel A, A is SalI and S is SacI. In panel B, S is SalI.
Figure 2B:
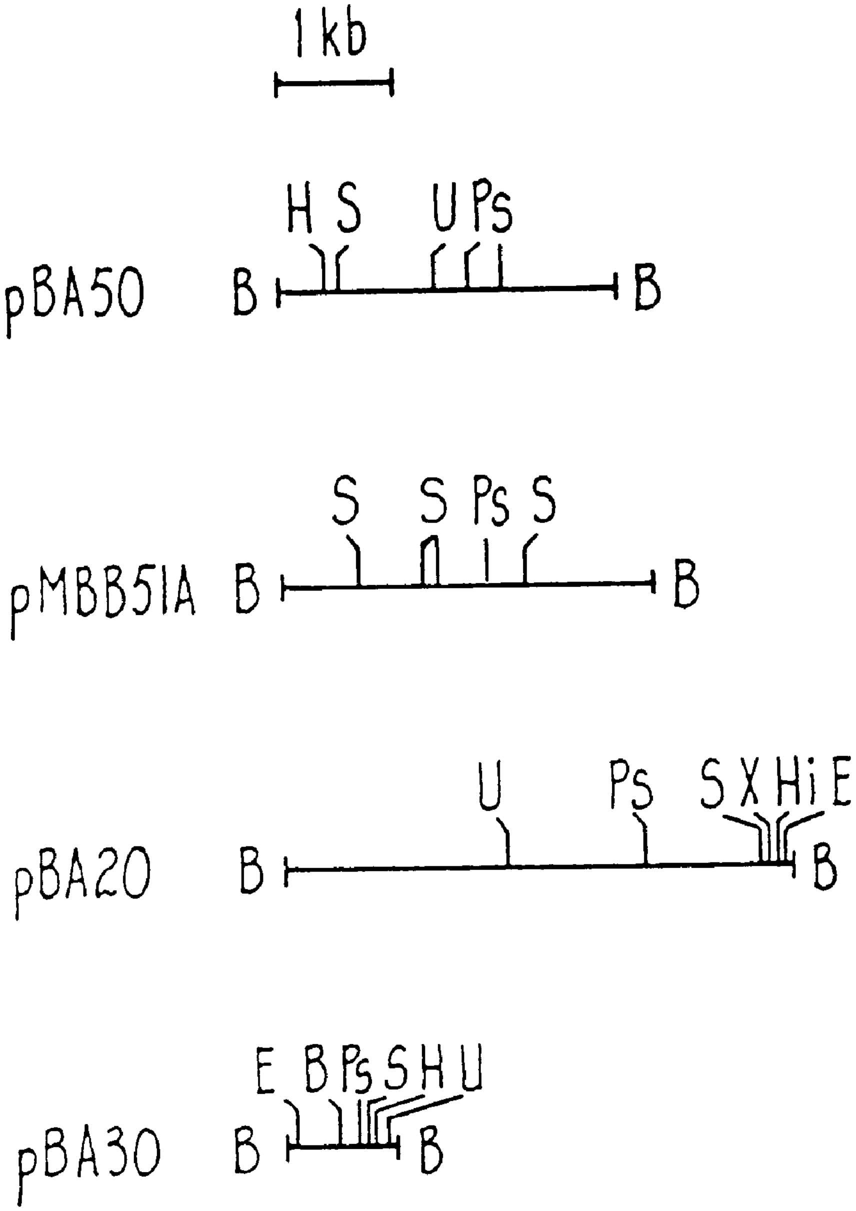

C. Restriction Mapping of Immunoreactive *Mycobacterium bovis* BCG DNA Recombinants The insert DNAs of four of the immunoreactive BCG recombinant DNA clones isolated using the TB sera were mapped with restriction endonucleases. FIG. 2, panel B, shows the genomic DNA restriction site maps deduced for the cloned BCG DNA in four recombinants, in which, A represents Sal I, B, BamH I, E, EcoR I, G, Bgl II, K, Kpn I, P, Pvu I, S, Sac I, X, Xho I. These restriction site maps were then compared with those constructed previously for the five immunodominant antigens of *M. tuberculosis/M. bovis* BCG (Young, et al., *Proc. Nati. Acad. Sci.*, U.S.A., 82:2583–2587 (1985); Husson, et al., *Proc. Natl. Acad. Sci.*, 84:1679–1683 (1987); Shinnick, et al., *Infect. Immun.*, 55, 7:1718–1721 (1987)) (FIG. 2, panel A). Since the restriction site maps shown in panels A and B have been drawn to the same scale, the differences between the two are apparent. There are no regions of similarity between the restriction site maps of immunoreactive BCG recombinant clones and those of the previously characterized immunodominant antigens of *M. tuberculosis/M. bovis* BCG. Therefore, one can conclude that the cloned BCG DNA inserts in the four recombinants are novel.

EXAMPLE II

Isolation and Characterization of a Gene Encoding a BCG Ion-motive ATPase

A. Identification of a Novel BCG Antigen

One of the four immunoreactive BCG clones, pMBB51A, revealed the presence of a protein of Mr 90 kD, on Western blot analysis using TB sera as well as anti-H37Rv polyclonal antiserum raised in rabbits (FIG. 3). Similar Western blot analysis of pMBB51A with a pool of a few anti-mycobacterial monoclonal antibodies (TB 23, TB 71, TB 72, TB 68, TB 78; Engers et al., *Infec. Immun.*, 48:603–605 (1985)) or with normal human sera did not reveal this immunoreactive protein of 90 kD. This confirms that pMBB51A encodes a BCG antigen which is different from those identified previously in BCG, thereby making it a novel antigen.

B. Determination of the Nucleotide Sequence of pMBB51A

In order to further characterize this novel BCG antigen, pMBB51A DNA insert was subjected to nucleotide sequencing. The BamH I-BamH I insert carried in pMBB51A was mapped for additional restriction enzyme cleavage sites. It was determined that there were at a minimum a single Pst I site and 3 Sal I sites in this sequence. Overlapping fragments derived from single and double digests of Sal I, BamH I and Sal I, BamH I and Pst I, and Pst I and Sal I, were subcloned into M13mp18 and M13mp19 vectors, in preparation for DNA sequence analysis. DNA sequencing was then carried out using commercially available kits such as the Sequenase system and the T7 system from Pharmacia. Oligonulceotides derived from the determined sequence were synthesized and used as primers to complete the sequence of the larger inserts. Several areas of compression were encountered during the sequencing and these were resolved by using dITP in the sequencing reactions, and by changing the reaction conditions. The complete nucleotide sequence of the pMBB51A insert DNA was determined by sequencing both the strands using dGTP as well as dITP. The DNA sequence of the pMBB51A insert was determined to be 3.25 kb long with a GC content of 67.1% and is shown in FIG. 4.

The determination of the DNA sequence of the 3.25 kb insert of clone pMBB51A (FIG. 4) permitted the elucidation of the amino acid sequence of the 90 kD BCG antigen. In FIG. 4, nucleotides are numbered from the left end of the pMBB51A insert DNA.

A search of pMBB51A insert DNA sequence for possible ORFs in all three reading frames revealed the longest ORF of 2286 bp encoding a polypeptide of 761 amino acids on one of the strands. The other strand was found to have a smaller URF of 1047 bp capable of encoding a polypeptide of 349 amino acids. The longest ORF encoding a 761 amino acid long protein corresponded to a deduced molecular weight of 79 kD which came closest to the immunoreactive BCG protein with apparent molecular weight of 90 kD, seen on the Western blot. The deduced amino acid sequence for this protein is given below the nucleotide sequence in FIG. 4.

The location of this ORF on the pMBB51A insert DNA was such that there were long stretches of flanking DNA sequences, devoid of any meaningful ORFs, present on either side. This precluded the expression of this ORF from the pBR322 Tet gene promoter and instead suggested that this ORF was being expressed from its own promoter in pMBB51A. This also suggested that *E. coli* may correctly utilize the *M. bovis* BCG transcription and translation start and stop sites in this gene.

Immediately upstream of the ORF, regulatory sequences closely matching the −35, −10 and Shine-Dalgarno sequences of *E. coli*, (Rosenberg, et al., *Annul. Rev. Genet*., 13:319–353 (1979)) were identified. The spacing between these three regulatory motifs was also very well conserved. Although the other mycobacterial promoters sequenced (Dale, et al., *Molecular Biology of the Mycobacteria*, chap. 8, 173–198 (1990)) show some differences from the *E. coli* consensus sequences in all the three regions −35, −10 and SD, the regulatory elements of pMBB51A DNA showed a maximum degree of sequence identity with *E. coli* in the −35 and SD sequence elements with a single mismatch in each element, and about 50% sequence identity in the Pribnow box. All the above features clearly indicated that this region is the promoter region for the mycobacterial gene contained in pMBB51A. The extent of similarity between this BCG promoter sequence and a typical *E. coli* promoter is remarkable and explains the functional activity of this promoter, unlike many other mycobacterial promoters, in *E. coli*. The translation initiation codon in this ORF was ATG at position 508 while a single translation termination codon TGA was identified at position 2790. Potential transcription termination structures capable of forming stem and loop conformations were identified in the region 3' to this ORF. The pMBB51A ORF thus represented a monocistronic gene rather than an operon. The promoter region of MBB51A gene is capable of directing gene expression in *E. coli* as well as in mycobacteria. This promoter sequence. is useful for directing expression of mycobacterial genes in *E. coli*. Further, this promoter sequence can also be used to express homologous and/or heterologous genes in a mycobacterium, thus providing a key element for the development of gene expression systems in mycobacteria.

In order to derive information about the possible biological function of the MBB51A protein, the amino acid sequence of this protein was used to search for homology against available sequences in the PIR Protein Database Release 20 (Table I) and a Genebank Nucleic Acid Database (Table II) using the Fast A suite of programmes written by (Lipman and Pearson, *Proc. Natl. Acad. Sci*., USA, 85:2 (1988)). The MBB51A protein sequence exhibited homology to a family of ion-motive ATPases from different organisms, ranging from bacteria to mammals. The 13 best scores from a search with ktuple 2 are shown in the upper panel of Table I and 10 best scores from a search with ktuple 1 are shown in the lower panel. In each case, MBB51A protein exhibited maximum homology (75.9% homology in a 593 amino acid overlap with 31.9% identity to a K+ transporting ATPase of *S. faecalis* (Solioz et al., 1987). The next best homology was observed with the B-chain of K+ transporting ATPase of *E. coli* (Hesse, et al., *Proc. Natl. Acad. Sci*., U.S.A., 81:4746–4750 (1984)) (68.8% homology in a 397 amino acid overlap with 24.2% identity). A lesser extent of homology was also seen with H+, Ca++ and Na+-ATPases from different organisms. The results of homology search thus indicated that MBB51A protein is an ion-motive ATPase of *M. bovis* BCG and is closely related to the other bacterial ion-motive ATPases. This is the first report of the cloning and identification of such an ATPase in mycobacteria. The BCG ion-motive ATPase showed homologies with other ion-motive ATPases with overlapping regions ranging in size from 593 amino acids in case of *S. faecalis* to 82 amino acids as in case of *L. donovani*, (Meade, et al., *Mol. Cell Biol*., 7, 3937–3946 (1987)), though most of the regions of sequence identity or conservation were localized in the C-terminal half of the MBB51A protein. Further, a region of 30 amino acids in the C-terminal half of MBB51A protein was found to be shared with most of these ATPases, thereby suggesting the functional importance of this region. Detailed alignment of MBB51A protein with the K+ ATPases of *S. faecalis* and *E. coli* also indicated that several residues were conserved between the three ATPases, including the ones that are invariant in all ATPases from bacteria to man.

TABLE I

RESULTS OF HOMOLOGY SEARCH OF MBB51A AMINO ACID SEQUENCE AGAINST PIR PROTEIN DATABASE

| LOCUS | SHORT DEFINITION | initn | opt |
|---|---|---|---|
| ktuple: 2 | | | |
| >A29576 | Potassium - transporting ATPase Streptococcus | 547 | 792 |
| >PWECBK | Potassium - transporting ATPase, β chain - *E. coli* | 314 | 270 |
| >A25939 | Proton - transporting ATPase - Neurospora | 168 | 186 |
| >A25823 | Proton - transporting ATPase - Yeast | 166 | 184 |
| >PWRBFC | Calcium - transporting ATPase, fast twitch skele | 152 | 158 |
| >PWRBSC | Calcium - transporting ATPase, slow twitch skele | 135 | 157 |
| >A25344 | Potassium - transporting ATPase - Rat | 78 | 155 |
| >RDEBHA | Mercuric reductase - *Shigella flexneri* plasmid | 99 | 142 |
| >RDPSHA | Mercuric reductase (transposon Tn501) | 74 | 124 |
| >RGPSHA | Mercuric resistance operon regulatory p | 79 | 109 |
| >A24639 | Sodium/potassium-transporting ATPase, alpha | 92 | 82 |
| >A24414 | Sodium/potassium-transporting ATPase, alpha | 92 | 82 |
| >B24862 | Sodium/potassium-transporting ATPase, beta | 83 | 82 |

The PJR protein data base (2378611 residues in 9124 sequences) was scanned with the FASTA program. The mean of the original initial score was 27.2 with a standard deviation of 6.9. Initial scores (initn) higher than 75.6 are 6 standard deviations above the average, a level of significance that usually indicates biological relatedness. Optimization (opt) generally will improve the initial score of related proteins by introducing gaps in the sequence. Unrelated sequences usually do not have their scores improved by optimization.

| | | | |
|---|---|---|---|
| ktuple: 1 | | | |
| >A29576 | potassium-transporting ATPase - Streptococcus | 744 | 792 |
| >PWECBK | potassium-transporting ATPase, β chain - Esche | 386 | 270 |
| >A25938 | Proton-transporting ATPase - *Neurospora crassa* | 310 | 186 |
| >A25823 | proton-transporting ATPase - Yeast (Saccharomy) | 317 | 184 |
| >B24639 | Sodium/potassium-transporting ATPase, alpha (+ | 158 | 163 |
| >A24639 | Sodium/potassium-transporting ATPase, alpha ch | 175 | 160 |
| >C24639 | Sodium/potassium-transporting ATPase, alpha (II | 192 | 159 |
| >PWRBFC | Calcium-transporting ATPase, fast twitch skele | 240 | 158 |
| >PWSHNA | Sodium/potassium-transporting ATPase, alpha skele | 214 | 158 |
| >A24414 | Sodium/potassium-transporting ATPase, alpha chain | 214 | 158 |

TABLE II

RESULTS OF HOMOLOGY SEARCH OF MBB51A AMINO ACID SEQUENCE AGAINST GENBANK NUCLEIC ACID SEQUENCE DATABASE

| LOCUS | SHORT DEFINITION | initn | opt |
|---|---|---|---|
| ktuple: 2 | | | |
| >STRATPK | *S. faecalis* K+ ATPase, complete cds. | 537 | 800 |
| >ECOKDPABC | *E. coli* kdpABC operon coding for Kdp-ATpase | 314 | 270 |
| >YSPPMA1A | *S. pombe* H+ ATPase, complete cds. | 135 | 188 |
| >NEUATPASE | *N. crassa* plasma membrane ATPase, complete | 133 | 186 |
| >NEUATPPM | *Neurospora crassa* plasma membrane H+ ATPase | 131 | 186 |
| >YSCPMA1 | Yeast PMA1 for plasma membrane ATPase | 166 | 184 |
| >M17889 | FIG. 2. N of *L. donovani* ATPase and | 166 | 170 |
| >M12898 | Rabbit fast twitch skeletal muscle Ca++ ATPas | 140 | 158 |
| >RABATPAC | Rabbit Ca + Mg dependent Ca++ ATPase mRNA, co | 142 | 157 |
| >NR1MER | Plasmid NR1 mercury resistance (mer) operon. | 100 | 143 |
| ktuple: 1 | | | |
| >STRATPK | *S. faecalis* K+ ATPase gene, complete cds. | 744 | 800 |
| >SYNCATPSB | Cyanobacterium Synechococcus 6301 DNA for AT | 379 | 422 |
| >ECOKDPABC | *E. coli kdpABC operon coding for Kdp-ATPase p* | 379 | 270 |
| >YSPPMA1A | *S. pombe* H+ ATPase gene, complete cds. | 275 | 188 |
| >NEUATPASE | *N. crassa* plasma membrane ATPase gene, comple | 311 | 186 |
| >NEUATPPM | *Neurospora crassa* plasma membrane H+ ATPase | 302 | 186 |
| >YSCPMA1 | Yeast PMA1 gene for plasma membrane ATPase | 317 | 184 |
| >JO4004 | *Leishmania donovani*, cation transporting ATP | 322 | 170 |
| >M17889 | FIG. 2. Nucleotide sequence of L. donovani | 306 | 170 |
| >RATATPA2 | Rat Na+, K+ ATPase alpha (+) isoform catalytic | 158 | 163 |

***

The KdpB protein of *E. coli* and possibly the *S. faecalis* K+ ATPase are members of E1E2-ATPases which are known to form an aspartyl phosphate intermediate, with cyclic transformation of the enzyme between phosphorylated and dephosphorylated species. By analogy to other ATPases, the phosphorylated Asp residue (D) (Furst, et al., *J. Biol. Chem.*, 260:50–52 (1985)) was identified at position 443 in the MBB51A ATPase. This residue is the first of a pentapeptide sequence DKTGT that has been conserved in ATPases from bacteria to man, and must form an essential element of the catalytic site. Similarly, proline (P) at position 400 in MBB51A ATPase was found to be an invariant amino acid in other ATPases and is predicted to be located in a membrane spanning domain. Such membrane buried proline residues have been hypothesized to be required for the reversible conformational changes necessary for the regulation of a transport channel (Brandl, et al., *Proc. Natl. Acad. Sci.*, U.S.A., 83:917–921 (1986)). In addition, other sequence motifs believed to be functionally important in other ion-motive ATPases were also found to be conserved in the MBB51A ATPase. These include a Gly (G) (Farley and Faller, *J. Biol. Chem.*, 260:3899–3901 (1985)) at position 521 and Ala (A) (Ohta, et al., *Proc. Natl. Acad. Sci.*, U.S.A., 83:2071–2075 (1986)) at position 646, and are shown in FIG. 5.

Since the MBB51A ATPase was homologous to membrane associated ATPases, characterization of the membrane associated helices in MBB51A protein was performed by computer algorithms. Using a hydropathy profile (Rao, et al., *Biochem. Biophys. Acta.*, 869:197–214 (1986)), seven transmembrane domains in the MBB51A protein were identified and are shown in Table III and FIG. 5. Nearly the same transmembrane domains were also identified using the hydrophobic moment plot (Eisenberg et al., *J. Mol. Biol.*, 179:125–142 (1984)) and are also shown in Table III and FIG. 5. The average size of a transmembrane domain is around 21 residues, because 21 residues coil into an α-helix approximately the thickness of the apolar position of a lipid bilayer (32 Å). This size of a transmembrane domain is, however, flexible within the range of a few amino acids, as determined by the functional properties of a given membrane-associated protein. The transmembrane domains identified in MBB51A protein, range in size from 20–37 residues. The first six transmembrane domains span the membrane only once, as indicated by both the hydropathy profile and the hydrophobic moment plot. The seventh transmembrane domain may traverse the membrane twice. These features along with the membrane buried proline (P) at position 400, are in accordance with the channel transport functions of ion-motive ATPases, involving a reversible change in the conformation of these proteins. Such transmembrane domains further define the intracellular and extracellular domains of this molecule. See FIG. 5.

TABLE III

| Transmembrane Domain in FIG. 5 | Eisenberg Method | Rao & Argos Method |
|---|---|---|
| 1 | 102–122 | 98–125 |
| 2 | 129–149 | 127–147 |
| 3 | 164–184 | 164–185 |
| 4 | 199–219 | 198–220 |
| 5 | 361–381 | 360–382 |
| 6 | 387–407 | 387–419 |
| 7 | 703–723 | 695–732 |

The hydropathy profile of MBB51A protein was nearly superimposable over that of *S. faecalis* K+ ATPase, even though the MBB51A ATPase has at the N-terminus, 154 extra amino acids, which were absent in *S. faecalis*. This clearly puts in evidence the strong evolutionary conservation of the broad domain structure between these two proteins, making it more likely for the two proteins to have a similar three dimensional structural organization.

Based on the hydropathy profile and secondary structure predictions, a schematic model of the MBB51A ATPase is presented in FIG. 5. This model comprises at least seven transmembrane domains which span the membrane once are indicated along with the respective amino acid positions in FIG. 5. This model further defines extracellular and intracellular domains of the MBB51A protein. Many of the residues which have been shown to be functionally important in other ion-motive ATPases and are also conserved in the MBB51A protein, are also shown. Of these, proline (P) at position 400 is membrane-buried whereas as aspartic acid(D) at 443, glycine (G) at 521 and alanine (A) at 646, face the cytoplasm.

Figure 6B:
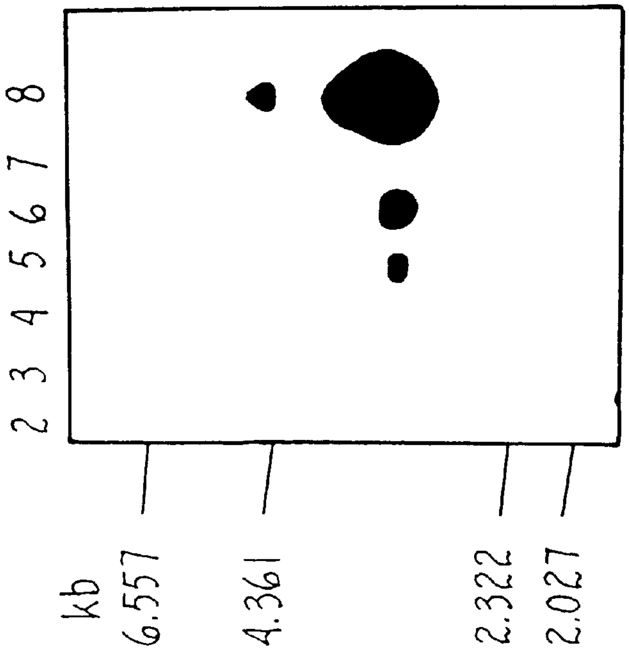
FIGS. 6A and 6B illustrate the results of Southern blot hybridization of BamHI digest of genomic DNAs from *M. bovis* BCG (lane 6), *M. tuberculosis* H37Rv (lane 5), *M. smegmatis* (lane 4) and *M. vaccae* (lane 3) using pMMB51A DNA insert (lane 8) as probe. Panel A shows ethidium bromide stained gel and panel B shows the results of Southern blot hybridization.
Figure 6A:
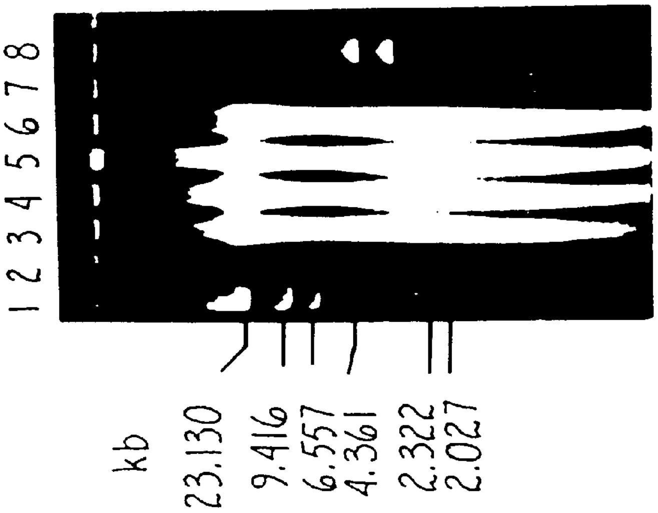

In order to determine whether the gene encoding MBB51A ion-motive ATPase is present in other mycobacterial strains related or unrelated to BCG, like the virulent strain *M. tuberculosis* H37Rv and other non-tuberculous, non-pathogenic mycobacteria like *M. vaccae* and *M. smegmatis*, Southern blot hybridization with genomic DNA from the above species was performed, using as probe BCG insert DNA from pMBB51A. As shown in FIG. 6, DNA hybridizable with the pMBB51A insert DNA was also present in *M. tuberculosis* H37Rv DNA but not in *M. smegmatis* and *M. vaccae*. This indicated that the *M. tuberculosis* H37Rv homologue of the pMBB51A gene has a similar genetic organization as seen in *M. bovis* BCG DNA, and is present on a 3.25 kb BamH I fragment.

The availability of novel *Mycobacterium bovis* BCG and/or *Mycobacterium tuberculosis* H37Rv antigens make it possible to address basic biochemical, immunological, diagnostic and therapeutic questions still unanswered about tuberculosis and *Mycobacterium tuberculosis*. For example, *Mycobacterium tuberculosis* specific antigenic determinants can be used to develop simple and specific seroepidemiological tests to screen human populations. Such serological tests are highly specific because of the use of antigenic determinants determined by the approaches described above and known to be unique to *Mycobacterium tuberculosis* H37Rv. Such serological tests are useful for early diagnosis of tuberculosis, thus permitting early treatment and limiting transmission of the disease from infected individuals to others.

Resistance to tuberculosis is provided by cell mediated immunity. The antigens identified here can be further used to determine which segments of these antigens are recognized by *Mycobacterium tuberculosis* specific T-cells. A mixture of peptides recognized by helper T-cells provides a specific skin test antigen for use in assessing the immunological status of patients and their contacts. A mixture of such peptides is also useful in evaluating rapidly the immunological efficacy of candidate vaccines. In addition peptides recognized by *Mycobacterium tuberculosis* specific T-cells can be components of a vaccine against the disease.

Knowledge of the complete nucleotide sequence of pMBB51A DNA insert provides a rich source of sequence information which can be used to design appropriate primers for PCR amplification of mycobacterial genomic DNA fragments. The ion-motive ATPase of BCG has areas of heavily conserved sequences (for, e.g., the ATP binding site) which are expected to be the same for all mycobacterial species and areas of sequence divergence (for, e.g., the N-terminal region) which are different in different mycobacterial species. Based on this knowledge primers can be designed either from the conserved regions or from the diverged regions to identify whether in a given sample the target DNA is mycobacterial versus non-mycobacterial, and in case of mycobacterial DNA, which mycobacterial species the DNA belongs.

Such amplification schemes are useful for the development of highly sensitive and specific PCR amplification based diagnostic procedures for mycobacteria. The observation that the 3.25 kb pMBB51A DNA insert is present in *Mycobacterium tuberculosis* H37Rv and *Mycobacterium bovis* BCG and is absent in avirulent *Mycobacterium vaccae* and *Mycobacterium smegmatis*, which have bearing on other aspects of the biological differences between these species, manifest in terms of virulence, growth characteristics and metabolism.

Recombinant vaccines can also be constructed by incorporating the DNA encoding all or part of the membrane-associated polypeptides of the invention into an appropriate vaccine vehicle. For example, all or part of the DNA encoding the 79 kD *Mycobacterium bovis* BCG protein or a portion of the protein can be incorporated into a vaccine vehicle capable of expressing the said DNA. Such a vaccine vehicle could be a virus for, e.g., vaccinia virus, etc., or a bacterium, e.g., mycobacteria, Salmonella, Vibrio, Bacillus, Yersinia, Bordetella, etc. to produce a vaccine capable of conferring long-lasting immunity on individuals to whom it is administered.

A special feature of the 79 kD BCG ion-motive ATPase is that it is a membrane bound antigen. Therefore, it can be used to link foreign DNA sequences encoding antigenic epitopes (B-cell epitopes or T-cell epitopes) of interest, with this gene or a portion of this gene in a manner which causes the foreign epitope to be used as an immunogen. Such linkages can be engineered into extracellular or intracellular domains of HBB51A protein, or into a combination of both types of domains. Engineering of immunogenic foreign epitopes into MBB51A DNA is accomplished by standard recombinant DNA methods known to those skilled in the art. Some of these methods involve use of unique restriction sites, in vitro mutagenesis and/or PCR-related methods. One such convenient method involves the use of a unique NdeI site at position 1090 in the MBB51A DNA where foreign DNA can be inserted. Grafting of epitopes on the cell surface induces rapid antibody response by virtue of the epitope being well-exposed on the bacterial cell, which in turn leads to direct activation of B cells. In addition, intracellular localization of an epitope induces B cell memory and a proficient T cell response. Examples of epitopes of interest known to be involved in the immune response to various pathogens include epitopes from *E. coli* LT toxin, foot and mouth disease virus, HIV, cholera toxin, etc.

Thus, the 79 kD antigen is useful in the design of recombinant vaccines against different pathogens. Such vaccines comprise a recombinant vaccine vehicle capable of expressing all or part of the 79 kD membrane-associated protein of mycobacteria, into which foreign epitopes have been engineered, such that the foreign epitopes are expressed on the outer surface and/or on the inner side of the cell membrane, thereby rendering the foreign epitopes immunogenic. The vaccine vehicle for this purpose may be a cultivable mycobacterium for, e.g., BCG. In these applications, the BCG ion-motive ATPase gene can be borne on a mycobacterial shuttle vector or alternately the foreign DNA encoding antigenic epitopes of the immunogenic polypeptides can be inserted into the mycobacterial genome via homologous recombination in the ion-motive ATPase gene or random integration. Such a process yields stable recombinant mycobacterial strains capable of expressing on their surface and/or in the cytoplasm antigenic sequences of interest, which can, for example, provide protection against a variety of infectious pathogens. Targeting of recombinant antigens to the cell-wall is attractive not only because of the high immunogenicity of mycobacterial cell-walls but, in addition, because of concerns with the introduction of a live vaccine in populations with a high prevalence of HIV seropositivity. Additionally, based on the MBB51A protein, a non-living but immunogenic recombinant cell surface subunit vaccine can also be developed to provide a useful alternative to live vaccines. Alternately, other bacterial, viral or protozoan vaccine vehicles could be transformed to generate such recombinant vaccines. Examples of potential vaccine vehicles include vaccinia virus, pox-viruses, Salmonella, Yerisinia, Vibrio, Bordetella, Bacillus, etc.

Further, using such an approach, multivalent recombinant vaccines which allow simultaneous expression of multiple protective epitopes/antigens of different pathogens, could also be designed.

Equivalents

Those skilled in the art will recognize, or be able to ascertain, using no more than routine experimentation, many equivalents to the specific materials and components described specifically herein. Such equivalents are intended to be encompassed in the scope of the following claims.

---

What is claimed is:

1. A recombinant nucleic acid encoding a chimeric polypeptide comprising a first polypeptide and all or part of a membrane associated polypeptide of a mycobacterium.

2. A nucleic acid of claim 1 wherein the said membrane associated mycobacterial polypeptide is encoded by nucleic acid which hybridizes with a nucleic acid probe having the sequence complementary to SEQ ID NO.:1 under conditions where said probe hybridizes with a single 3.25 kb BamHI fragment from *M. bovis* BCG and *M. tuberculosis* H37Rv DNA, but does not hybridize with BamHI-digested DNA from either *M. smegmatis* or *M vaccae.*

3. The nucleic acid of claim 2 wherein said mycobacterium is selected from the group consisting of *M tuberculosis, M. leprae, M. africanum, M. microti, M. avium, M. intracellulare, M. scrofulaceum*, and strains of *M. bovis* other than *M bovis* BCG.

4. The nucleic acid of said claim 1 wherein said first polypeptide comprises an immunogenic polypeptide.

5. An expression host comprising the nucleic acid of claim 1.

6. The expression host of claim 5 wherein said expression host is selected from the group consisting of a virus and a bacterium.

7. The expression host of claim 6 wherein said virus comprises a poxvirus.

8. The expression host of claim 6 wherein said bacterium is selected from the group consisting of Salmonella, Yersinia, Vibrio, Bordetella, and Bacillus.

9. A chimeric polypeptide encoded by the nucleic acid of claim 1.

10. A composition comprising the chimeric polypeptide of claim 9 in combination with a physiologically acceptable carrier.

* * * * *

SEQUENCE LISTING

```
(1) GENERAL INFORMATION:

   (iii) NUMBER OF SEQUENCES: 2


(2) INFORMATION FOR SEQ ID NO:1:

     (i) SEQUENCE CHARACTERISTICS:
          (A) LENGTH: 3250 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 508..2790

    (xi) SEQUENCE DESCRIPTION: SEQ ID NO:1:

GGATCCCGCG GTCATCGATC GGGTCAAACA CCGCCTCGAC GGGTTCACGC TGGCGCCGCT      60

GTCCACCGCC GCGGGAGGTG GTGGCCGGCA GCCACGCATC TACTACGGCA CCATCCTGAC     120

CGGTGACCAA TACCTTCACT GCGAGCGCAC CCGCAACCGG CTGCACCACG AACTCGGCGG     180

TATGGCCGTC GAAATGGAAG GCGGTGCGGT GGCGCAAATC TGCGCGTCCT TCGATATCCC     240

ATGGCTGGTC ATTCGCGCGC TCTCCGATCT CGCCGGAGCC GATTCGGGGG TGGACTTCAA     300

TCGGTTTGTC GGCGAGGTGG CGGCCAGTTC GGCCCGCGTT CTGCTGCGCT TGCTGCCGGT     360

GTTGACGGCC TGTTGAAGAC GACTATCCGC CGGTGCGTTC ACCGCGTCAG GCGGCTTCGG     420

TGAGGTGAGT AATTTGGTCA TTAACTTGGT CATGCCGCCG CCGATGTTGA GCGGAGGCCA     480

CAGGTCGGCC GGAAGTGAGG AGCCACG ATG ACG GCG GCC GTG ACC GGT GAA        531
                              Met Thr Ala Ala Val Thr Gly Glu
                                1               5

CAC CAC GCG AGT GTG CAG CGG ATA CAA CTC AGA ATC AGC GGG ATG TCG      579
His His Ala Ser Val Gln Arg Ile Gln Leu Arg Ile Ser Gly Met Ser
     10                  15                  20

TGC TCT GCG TGC GCC CAC CGT GTG GAA TCG ACC CTC AAC AAG CTG CCG      627
```

-continued

```
Cys Ser Ala Cys Ala His Arg Val Glu Ser Thr Leu Asn Lys Leu Pro
 25                 30                  35                  40

GGG GTT CGG GCA GCT GTG AAC TTC GGC ACC CGG GTG GCA ACC ATC GAC      675
Gly Val Arg Ala Ala Val Asn Phe Gly Thr Arg Val Ala Thr Ile Asp
                45                  50                  55

ACC AGC GAG GCG GTC GAC GCT GCC GCG CTG TGC CAG GCG GTC CGC CGC      723
Thr Ser Glu Ala Val Asp Ala Ala Ala Leu Cys Gln Ala Val Arg Arg
            60                  65                  70

GCG GGC TAT CAG GCC GAT CTG TGC ACG GAT GAC GGT CGG AGC GCG AGT      771
Ala Gly Tyr Gln Ala Asp Leu Cys Thr Asp Asp Gly Arg Ser Ala Ser
        75                  80                  85

GAT CCG GAC GCC GAC CAC GCT CGA CAG CTG CTG ATC CGG CTA GCG ATC      819
Asp Pro Asp Ala Asp His Ala Arg Gln Leu Leu Ile Arg Leu Ala Ile
     90                  95                 100

GCC GCC GTG CTG TTT GTG CCC GTG GCC GAT CTG TCG GTG ATG TTT GGG      867
Ala Ala Val Leu Phe Val Pro Val Ala Asp Leu Ser Val Met Phe Gly
105                 110                 115                 120

GTC GTG CCT GCC ACG CGC TTC ACC GGC TGG CAG TGG GTG CTA AGC GCG      915
Val Val Pro Ala Thr Arg Phe Thr Gly Trp Gln Trp Val Leu Ser Ala
                125                 130                 135

CTG GCA CTG CCG GTC GTG ACC TGG GCG GCG TGG CCG TTT CAC CGC GTT      963
Leu Ala Leu Pro Val Val Thr Trp Ala Ala Trp Pro Phe His Arg Val
            140                 145                 150

GCG ATG CGC AAC GCC CGC CAC CAC GCC GCC TCC ATG GAG ACG CTA ATC     1011
Ala Met Arg Asn Ala Arg His His Ala Ala Ser Met Glu Thr Leu Ile
        155                 160                 165

TCG GTC GGT ATC ACG GCC GCC ACG ATC TGG TCG CTG TAC ACC GTC TTC     1059
Ser Val Gly Ile Thr Ala Ala Thr Ile Trp Ser Leu Tyr Thr Val Phe
    170                 175                 180

GGC AAT CAC TCG CCC ATC GAG CGC AGC GGC ATA TGG CAG GCG CTG CTG     1107
Gly Asn His Ser Pro Ile Glu Arg Ser Gly Ile Trp Gln Ala Leu Leu
185                 190                 195                 200

GGA AGC GAT GCT ATT TAT TTC GAG GTC GCG GCG GGT GTC ACG GTG TTC     1155
Gly Ser Asp Ala Ile Tyr Phe Glu Val Ala Ala Gly Val Thr Val Phe
                205                 210                 215

GTG CTG GTG GGG CGG TAT TTC GAG GCG CGC GCC AAG TCG CAG GCG GGC     1203
Val Leu Val Gly Arg Tyr Phe Glu Ala Arg Ala Lys Ser Gln Ala Gly
            220                 225                 230

AGT GCG CTG AGA GCC TTG GCG GCG CTG AGC GCC AAG GAA GTA GCC GTC     1251
Ser Ala Leu Arg Ala Leu Ala Ala Leu Ser Ala Lys Glu Val Ala Val
        235                 240                 245

CTG CTA CCG GAT GGG TCG GAG ATG GTC ATC CCG GCC GAC GAA CTC AAA     1299
Leu Leu Pro Asp Gly Ser Glu Met Val Ile Pro Ala Asp Glu Leu Lys
    250                 255                 260

GAA CAG CAG CGC TTC GTG GTG CGT CCA GGG CAG ATA GTT GCC GCC GAC     1347
Glu Gln Gln Arg Phe Val Val Arg Pro Gly Gln Ile Val Ala Ala Asp
265                 270                 275                 280

GGC CTC GCC GTC GAC GGG TCC GCT GCG GTC GAC ATG AGC GCG ATG ACC     1395
Gly Leu Ala Val Asp Gly Ser Ala Ala Val Asp Met Ser Ala Met Thr
                285                 290                 295

GGC GAG GCC AAA CCG ACC CGG GTG CGT CCG GGG GGG CAG GTC ATC GGC     1443
Gly Glu Ala Lys Pro Thr Arg Val Arg Pro Gly Gly Gln Val Ile Gly
            300                 305                 310

GGC ACC ACA GTG CTT GAC GGC CGG CTG ATC GTG GAG GCG GCC GCG GTG     1491
Gly Thr Thr Val Leu Asp Gly Arg Leu Ile Val Glu Ala Ala Ala Val
        315                 320                 325

GGC GCC GAC ACC CAG TTC GCC GGA ATG GTC CGC CTC GTT GAG CAA GCG     1539
Gly Ala Asp Thr Gln Phe Ala Gly Met Val Arg Leu Val Glu Gln Ala
    330                 335                 340
```

-continued

```
CAG GCG CAA AAG GCC GAC GCA CAG CGA CTA GCC GAC CGG ATC TCC TCG     1587
Gln Ala Gln Lys Ala Asp Ala Gln Arg Leu Ala Asp Arg Ile Ser Ser
345                 350                 355                 360

GTG TTT GTT CCC GCT GTG TTG GTT ATC GCG GCA CTA ACC GCA GCC GGA     1635
Val Phe Val Pro Ala Val Leu Val Ile Ala Ala Leu Thr Ala Ala Gly
                365                 370                 375

TGG CTA ATC GCC GGG GGA CAA CCC GAC CGT GCC GTC TCG GCC GCA CTC     1683
Trp Leu Ile Ala Gly Gly Gln Pro Asp Arg Ala Val Ser Ala Ala Leu
            380                 385                 390

GCC GTG CTT GTC ATC GCC TGC CCG TGT GCC CTG GGG CTG GCG ACT CCG     1731
Ala Val Leu Val Ile Ala Cys Pro Cys Ala Leu Gly Leu Ala Thr Pro
        395                 400                 405

ACC GCG ATG ATG GTG GCC TCT GGT CGC GGT GCC CAG CTC GGA ATA TTT     1779
Thr Ala Met Met Val Ala Ser Gly Arg Gly Ala Gln Leu Gly Ile Phe
    410                 415                 420

CTG AAG GGC TAC AAA TCG TTG GAG GCC ACC CGC GCG GTG GAC ACC GTC     1827
Leu Lys Gly Tyr Lys Ser Leu Glu Ala Thr Arg Ala Val Asp Thr Val
425                 430                 435                 440

GTC TTC GAC AAG ACC GGC ACC CTG ACG ACG GGC CGG CTG CAG GTC AGT     1875
Val Phe Asp Lys Thr Gly Thr Leu Thr Thr Gly Arg Leu Gln Val Ser
                445                 450                 455

GCG GTG ACC GCG GCA CCG GGC TGG GAG GCC GAC CAG GTG CTC GCC TTG     1923
Ala Val Thr Ala Ala Pro Gly Trp Glu Ala Asp Gln Val Leu Ala Leu
            460                 465                 470

GCC GCG ACC GTG GAA GCC GCG TCC GAG CAC TCG GTG GCG CTC GCG ATC     1971
Ala Ala Thr Val Glu Ala Ala Ser Glu His Ser Val Ala Leu Ala Ile
        475                 480                 485

GCC GCG GCA ACG ACT CGG CGA GAC GCG GTC ACC GAC TTT CGC GCC ATA     2019
Ala Ala Ala Thr Thr Arg Arg Asp Ala Val Thr Asp Phe Arg Ala Ile
    490                 495                 500

CCC GGC CGC GGC GTC AGC GGC ACC GTG TCC GGG CGG GCG GTA CGG GTG     2067
Pro Gly Arg Gly Val Ser Gly Thr Val Ser Gly Arg Ala Val Arg Val
505                 510                 515                 520

GGC AAA CCG TCA TGG ATC GGG TCC TCG TCG TGC CAC CCC AAC ATG CGC     2115
Gly Lys Pro Ser Trp Ile Gly Ser Ser Ser Cys His Pro Asn Met Arg
                525                 530                 535

GCG GCC CGG CGC CAC GCC GAA TCG CTG GGT GAG ACG GCC GTA TTC GTC     2163
Ala Ala Arg Arg His Ala Glu Ser Leu Gly Glu Thr Ala Val Phe Val
            540                 545                 550

GAG GTC GAC GGC GAA CCA TGC GGG GTC ATC GCG GTC GCC GAC GCC GTC     2211
Glu Val Asp Gly Glu Pro Cys Gly Val Ile Ala Val Ala Asp Ala Val
        555                 560                 565

AAG GAC TCG GCG CGA GAC GCC GTG GCC GCC CTG GCC GAT CGT GGT CTG     2259
Lys Asp Ser Ala Arg Asp Ala Val Ala Ala Leu Ala Asp Arg Gly Leu
    570                 575                 580

CGC ACC ATG CTG TTG ACC GGT GAC AAT CCC GAA TCG GCG GCG GCC GTG     2307
Arg Thr Met Leu Leu Thr Gly Asp Asn Pro Glu Ser Ala Ala Ala Val
585                 590                 595                 600

GCT ACT CGC GTC GGC ATC GAC GAG GTG ATC GCC GAC ATC CTG CCG GAA     2355
Ala Thr Arg Val Gly Ile Asp Glu Val Ile Ala Asp Ile Leu Pro Glu
                605                 610                 615

GGC AAG GTC GAT GTC ATC GAG CAG CTA CGC GAC CGC GGA CAT GTC GTC     2403
Gly Lys Val Asp Val Ile Glu Gln Leu Arg Asp Arg Gly His Val Val
            620                 625                 630

GCC ATG GTC GGT GAC GGC ATC AAC GAC GGA CCC GCA CTG GCC CGT GCC     2451
Ala Met Val Gly Asp Gly Ile Asn Asp Gly Pro Ala Leu Ala Arg Ala
        635                 640                 645

GAT CTA GGC ATG GCC ATC GGG CGC GGC ACG GAC GTC GCG ATC GGT GCC     2499
Asp Leu Gly Met Ala Ile Gly Arg Gly Thr Asp Val Ala Ile Gly Ala
    650                 655                 660
```

-continued

```
GCC GAC ATC ATC TTG GTC CGC GAC CAC CTC GAC GTT GTA CCC CTT GCG     2547
Ala Asp Ile Ile Leu Val Arg Asp His Leu Asp Val Val Pro Leu Ala
665                 670                 675                 680

CTT GAC CTG GCA AGG GCC ACG ATG CGC ACC GTC AAA CTC AAC ATG GTC     2595
Leu Asp Leu Ala Arg Ala Thr Met Arg Thr Val Lys Leu Asn Met Val
                685                 690                 695

TGG GCA TTC GGA TAC AAC ATC GCC GCG ATT CCC GTC GCC GCT GCC GGA     2643
Trp Ala Phe Gly Tyr Asn Ile Ala Ala Ile Pro Val Ala Ala Ala Gly
            700                 705                 710

CTG CTC AAC CCC CTG GTG GCC GGT GCG GCC ATG GCG TTC TCA TCG TTC     2691
Leu Leu Asn Pro Leu Val Ala Gly Ala Ala Met Ala Phe Ser Ser Phe
        715                 720                 725

TTC GTG GTC TCA AAC AGC TTG CGG TTG CGC AAA TTT GGG CGA TAC CCG     2739
Phe Val Val Ser Asn Ser Leu Arg Leu Arg Lys Phe Gly Arg Tyr Pro
    730                 735                 740

CTA GGC TGC GGA ACC GTC GGT GGG CCA CAA ATG ACC GCG CCG TCG TCC     2787
Leu Gly Cys Gly Thr Val Gly Gly Pro Gln Met Thr Ala Pro Ser Ser
745                 750                 755                 760

GCG TGATGCGTTG TCGGGCAACA CGATATCGGG CTCAGCGGCG ACCGCATCCG          2840
Ala

GTCTCGGCCG AGGACCAGAG GCGCTTCGCC ACACCATGAT TGCCAGGACC GCGCCGATCA   2900

CCACCGGCAG ATGAGTCAAA ATCCGCGTGG TGCTGACCGC GCCGGACAGC GCATCCACAA   2960

TCACATAGCC GGTCAGTATG GCGACGAACG CCGTCAGAAC ACCGGCCAGG CCGGCGGCGG   3020

CGCTCGGCCA TAGCGCCGCG CCCACCATGA TCACACCGAG CGCAATCGAC CACGACGTGA   3080

CTCGTTGAGC AAGTGGGTGC CGGCACCCGT CGGGTGCTGA TGGGTCAGGC CGACGTCTAG   3140

GCCAAACCCC TGCACGGTGC CCAGGGCGAT CTGCGCGATG CCCACGCACA GCAACGCCCA   3200

ACGTCGCCAG GTCATCGGTG AATGTTGCCG CCGCGGCGCC CGGCGGATCC              3250
```

(2) INFORMATION FOR SEQ ID NO:2:

(i) SEQUENCE CHARACTERISTICS:
(A) LENGTH: 761 amino acids
(B) TYPE: amino acid
(D) TOPOLOGY: linear (ii) MOLECULE TYPE: protein (xi) SEQUENCE DESCRIPTION: SEQ ID NO:2:

```
Met Thr Ala Ala Val Thr Gly Glu His His Ala Ser Val Gln Arg Ile
  1               5                  10                  15

Gln Leu Arg Ile Ser Gly Met Ser Cys Ser Ala Cys Ala His Arg Val
            20                  25                  30

Glu Ser Thr Leu Asn Lys Leu Pro Gly Val Arg Ala Ala Val Asn Phe
        35                  40                  45

Gly Thr Arg Val Ala Thr Ile Asp Thr Ser Glu Ala Val Asp Ala Ala
    50                  55                  60

Ala Leu Cys Gln Ala Val Arg Arg Ala Gly Tyr Gln Ala Asp Leu Cys
 65                  70                  75                  80

Thr Asp Asp Gly Arg Ser Ala Ser Asp Pro Asp Ala Asp His Ala Arg
                85                  90                  95

Gln Leu Leu Ile Arg Leu Ala Ile Ala Ala Val Leu Phe Val Pro Val
            100                 105                 110

Ala Asp Leu Ser Val Met Phe Gly Val Val Pro Ala Thr Arg Phe Thr
        115                 120                 125

Gly Trp Gln Trp Val Leu Ser Ala Leu Ala Leu Pro Val Val Thr Trp
```

-continued

```
    130                 135                 140

Ala Ala Trp Pro Phe His Arg Val Ala Met Arg Asn Ala Arg His His
145                 150                 155                 160

Ala Ala Ser Met Glu Thr Leu Ile Ser Val Gly Ile Thr Ala Ala Thr
                165                 170                 175

Ile Trp Ser Leu Tyr Thr Val Phe Gly Asn His Ser Pro Ile Glu Arg
            180                 185                 190

Ser Gly Ile Trp Gln Ala Leu Leu Gly Ser Asp Ala Ile Tyr Phe Glu
        195                 200                 205

Val Ala Ala Gly Val Thr Val Phe Val Leu Val Gly Arg Tyr Phe Glu
    210                 215                 220

Ala Arg Ala Lys Ser Gln Ala Gly Ser Ala Leu Arg Ala Leu Ala Ala
225                 230                 235                 240

Leu Ser Ala Lys Glu Val Ala Val Leu Leu Pro Asp Gly Ser Glu Met
                245                 250                 255

Val Ile Pro Ala Asp Glu Leu Lys Glu Gln Gln Arg Phe Val Val Arg
            260                 265                 270

Pro Gly Gln Ile Val Ala Ala Asp Gly Leu Ala Val Asp Gly Ser Ala
        275                 280                 285

Ala Val Asp Met Ser Ala Met Thr Gly Glu Ala Lys Pro Thr Arg Val
    290                 295                 300

Arg Pro Gly Gly Gln Val Ile Gly Gly Thr Thr Val Leu Asp Gly Arg
305                 310                 315                 320

Leu Ile Val Glu Ala Ala Ala Val Gly Ala Asp Thr Gln Phe Ala Gly
                325                 330                 335

Met Val Arg Leu Val Glu Gln Ala Gln Ala Gln Lys Ala Asp Ala Gln
            340                 345                 350

Arg Leu Ala Asp Arg Ile Ser Ser Val Phe Val Pro Ala Val Leu Val
        355                 360                 365

Ile Ala Ala Leu Thr Ala Ala Gly Trp Leu Ile Ala Gly Gly Gln Pro
    370                 375                 380

Asp Arg Ala Val Ser Ala Ala Leu Ala Val Leu Val Ile Ala Cys Pro
385                 390                 395                 400

Cys Ala Leu Gly Leu Ala Thr Pro Thr Ala Met Met Val Ala Ser Gly
                405                 410                 415

Arg Gly Ala Gln Leu Gly Ile Phe Leu Lys Gly Tyr Lys Ser Leu Glu
            420                 425                 430

Ala Thr Arg Ala Val Asp Thr Val Val Phe Asp Lys Thr Gly Thr Leu
        435                 440                 445

Thr Thr Gly Arg Leu Gln Val Ser Ala Val Thr Ala Ala Pro Gly Trp
    450                 455                 460

Glu Ala Asp Gln Val Leu Ala Leu Ala Ala Thr Val Glu Ala Ala Ser
465                 470                 475                 480

Glu His Ser Val Ala Leu Ala Ile Ala Ala Ala Thr Thr Arg Arg Asp
                485                 490                 495

Ala Val Thr Asp Phe Arg Ala Ile Pro Gly Arg Gly Val Ser Gly Thr
            500                 505                 510

Val Ser Gly Arg Ala Val Arg Val Gly Lys Pro Ser Trp Ile Gly Ser
        515                 520                 525

Ser Ser Cys His Pro Asn Met Arg Ala Ala Arg Arg His Ala Glu Ser
    530                 535                 540

Leu Gly Glu Thr Ala Val Phe Val Glu Val Asp Gly Glu Pro Cys Gly
545                 550                 555                 560
```

-continued

```
Val Ile Ala Val Ala Asp Ala Val Lys Asp Ser Ala Arg Asp Ala Val
                565                 570                 575

Ala Ala Leu Ala Asp Arg Gly Leu Arg Thr Met Leu Leu Thr Gly Asp
            580                 585                 590

Asn Pro Glu Ser Ala Ala Ala Val Ala Thr Arg Val Gly Ile Asp Glu
        595                 600                 605

Val Ile Ala Asp Ile Leu Pro Glu Gly Lys Val Asp Val Ile Glu Gln
    610                 615                 620

Leu Arg Asp Arg Gly His Val Val Ala Met Val Gly Asp Gly Ile Asn
625                 630                 635                 640

Asp Gly Pro Ala Leu Ala Arg Ala Asp Leu Gly Met Ala Ile Gly Arg
                645                 650                 655

Gly Thr Asp Val Ala Ile Gly Ala Ala Asp Ile Ile Leu Val Arg Asp
            660                 665                 670

His Leu Asp Val Val Pro Leu Ala Leu Asp Leu Ala Arg Ala Thr Met
        675                 680                 685

Arg Thr Val Lys Leu Asn Met Val Trp Ala Phe Gly Tyr Asn Ile Ala
    690                 695                 700

Ala Ile Pro Val Ala Ala Ala Gly Leu Leu Asn Pro Leu Val Ala Gly
705                 710                 715                 720

Ala Ala Met Ala Phe Ser Ser Phe Phe Val Val Ser Asn Ser Leu Arg
                725                 730                 735

Leu Arg Lys Phe Gly Arg Tyr Pro Leu Gly Cys Gly Thr Val Gly Gly
            740                 745                 750

Pro Gln Met Thr Ala Pro Ser Ser Ala
        755                 760
```